(12) United States Patent
Hossainy et al.

(10) Patent No.: US 8,337,874 B2
(45) Date of Patent: *Dec. 25, 2012

(54) PRIMER COATING OF INORGANIC MATERIAL FOR IMPLANTABLE DEVICES

(75) Inventors: Syed F. A. Hossainy, Hayward, CA (US); Stephen D. Pacetti, San Jose, CA (US); Keith E. Fong, Palo Alto, CA (US); Vinayak Bhat, Sunnyvale, CA (US); Deborra Sanders Millare, San Jose, CA (US); Judy A. Guruwaiya, San Jose, CA (US); Daryush Mirzaee, Sunnyvale, CA (US); Evgenia Mandrusov, Campbell, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/723,534

(22) Filed: Mar. 12, 2010

(65) Prior Publication Data

US 2010/0198339 A1 Aug. 5, 2010

Related U.S. Application Data

(60) Division of application No. 10/751,289, filed on Jan. 2, 2004, now Pat. No. 7,820,190, which is a continuation of application No. 09/750,595, filed on Dec. 28, 2000, now Pat. No. 6,790,228.

(51) Int. Cl.
*A61F 13/00* (2006.01)
*A61F 2/06* (2006.01)

(52) U.S. Cl. ..... 424/422; 623/1.15; 623/1.42; 623/1.44; 623/1.46

(58) Field of Classification Search .............. None
See application file for complete search history.

(56) References Cited

U.S. PATENT DOCUMENTS

| 4,580,568 | A | * | 4/1986 | Gianturco | 606/198 |
|---|---|---|---|---|---|
| 4,733,665 | A | | 3/1988 | Palmaz | |
| 4,886,062 | A | | 12/1989 | Wiktor | |
| 5,006,313 | A | * | 4/1991 | Swedberg | 204/601 |
| 5,053,048 | A | * | 10/1991 | Pinchuk | 623/1.43 |
| 5,272,012 | A | | 12/1993 | Opolski | |
| 5,423,929 | A | * | 6/1995 | Doyle et al. | 156/73.1 |
| 5,464,650 | A | | 11/1995 | Berg et al. | |
| 5,573,934 | A | * | 11/1996 | Hubbell et al. | 435/177 |
| 5,824,049 | A | | 10/1998 | Ragheb et al. | |
| 5,962,620 | A | | 10/1999 | Reich et al. | |

(Continued)

FOREIGN PATENT DOCUMENTS

DE 199 13 978 9/2000

(Continued)

OTHER PUBLICATIONS

European Search Report for 01994454.5 mailed Apr. 10, 2007, 4 pgs.

(Continued)

*Primary Examiner* — Fereydoun G Sajjadi
*Assistant Examiner* — Casey Hagopian
(74) *Attorney, Agent, or Firm* — Squire Sanders (US) LLP

(57) ABSTRACT

Coatings for implantable devices or endoluminal prosthesis, such as stents, are provided, including a method of forming the coatings. The coatings can be used for the delivery of an active ingredient or a combination of active ingredients.

17 Claims, 6 Drawing Sheets

U.S. PATENT DOCUMENTS

| | | | |
|---|---|---|---|
| 5,968,091 A * | 10/1999 | Pinchuk et al. | 623/1.16 |
| 6,096,726 A * | 8/2000 | Opolski | 514/53 |
| 6,187,024 B1 * | 2/2001 | Boock et al. | 606/191 |
| 6,335,029 B1 | 1/2002 | Kamath et al. | |
| 6,451,373 B1 | 9/2002 | Hossainy et al. | |
| 6,712,845 B2 | 3/2004 | Hossainy | |
| 6,790,228 B2 * | 9/2004 | Hossainy et al. | 623/1.46 |
| 6,908,624 B2 | 6/2005 | Hossainy et al. | |
| 2002/0123801 A1 | 9/2002 | Pacetti et al. | |
| 2004/0220665 A1 | 11/2004 | Hossainy et al. | |
| 2005/0233062 A1 | 10/2005 | Hossainy et al. | |

FOREIGN PATENT DOCUMENTS

| | | |
|---|---|---|
| EP | 0 879 595 | 11/1998 |
| EP | 0 970 711 | 1/2000 |
| EP | 0 985 413 | 3/2000 |
| JP | 10-305105 | 11/1998 |
| JP | 2000-051367 | 2/2000 |
| WO | WO 00/07574 | 2/2000 |
| WO | WO 01/43788 | 6/2001 |
| WO | WO 01/45763 | 6/2001 |
| WO | WO 01/87372 | 11/2001 |
| WO | WO 02/26139 | 4/2002 |
| WO | WO 02/056790 | 7/2002 |
| WO | WO 02/058753 | 8/2002 |
| WO | WO 02/074194 | 9/2002 |
| WO | WO 03/022323 | 3/2003 |
| WO | WO 03/035131 | 5/2003 |
| WO | WO 03/082368 | 10/2003 |
| WO | WO 03/090818 | 11/2003 |
| WO | WO 2005/004945 | 1/2005 |

OTHER PUBLICATIONS

JPO Notice of the Reason for Refusal for application 2002-559086, mailed Jun. 17, 2008, 4 pgs.

International Search Report and Written Opinion for PCT/US2004/017060, filed May 28, 2004, mailed Dec. 30, 2004, 10 pgs.

Translation of JPO Notice of the Reason for Refusal for application 2002-559086, mailed Jun. 17, 2008, 5 pgs.

Cox et al., "Effect of local delivery of heparin and methotrexate on neointimal proliferation in stented porcine coronary arteries", Coronary Artery Disease vol. 3, No. 3, pp. 237-248 (1992).

Hunter et al., "Local delivery of chemotherapy: a supplement to existing cancer treatments a case for surgical pastes and coated stents", Advanced Drug Delivery Reviews 26, pp. 199-207 (1997).

Dichek et al, "Seeding of Intravascular Stents with Genetically Engineered Endothelial Cells", Circulation vol. 80, No. 5, pp. 1347-1353 (1989).

Schwartz et al., "Restenosis After Ballon Angioplasty", Circulation vol. 82, No. 6, pp. 2190-2200 (1990).

Schwartz et al., "Restenosis and the Proportional Neointimal Response to Coronary Artery Injury: Results in a Porcine Model", JACC vol. 19, No. 2, pp. 267-274 (1992).

Degertekin et al., "Persistent Inhibition of Neointimal Hyperplasia After Sirolimus-Eluting Stent Implantation: Long-Term Clinical, Angiographic, and Intravascular Ultrasound Follow-Up", Circulation 106, pp. 1610-1613 Abstract 1 pg. (2002).

Forrest et al., "Brillouin Light Scattering Determination of the Glass Transition in Thin, Freely-Standing Poly (styrene) Films", Met. Res. Soc. Symp. Proc. vol. 407, pp. 131-136 (1996).

Sousa et al., "Lack of Neointimal Proliferation After Implantation of Sirolimus-Coated Stents in Human Coronary Arteries", Circulation 103, pp. 192-195 (2001).

Sousa et al., "Two-Year Angiographic and Intravascular Ultrasound Follow-Up After Implantation of Sirolimus-Eluting Stents in Human Coronary Arteries", Circulation 107, pp. 381-383 (2003).

Tokoh et al., "Glass Transition Temperature of Ethylene-Vinyl Alcohol Copolymers", Chemistry Express vol. 2, No. 9, pp. 575-578 (1987).

* cited by examiner

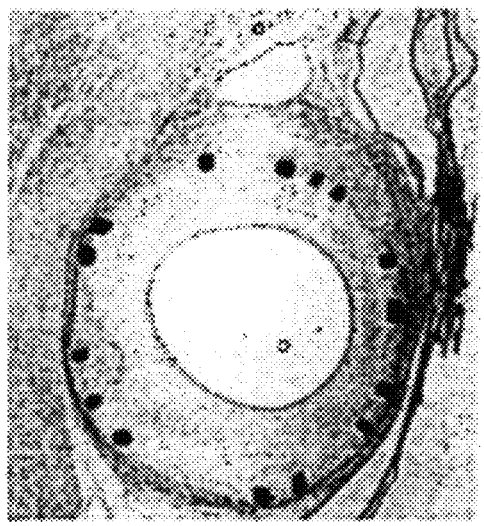 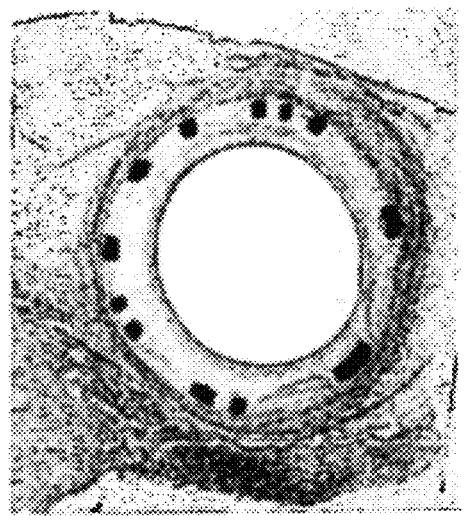
FIG. 6A  FIG. 6B
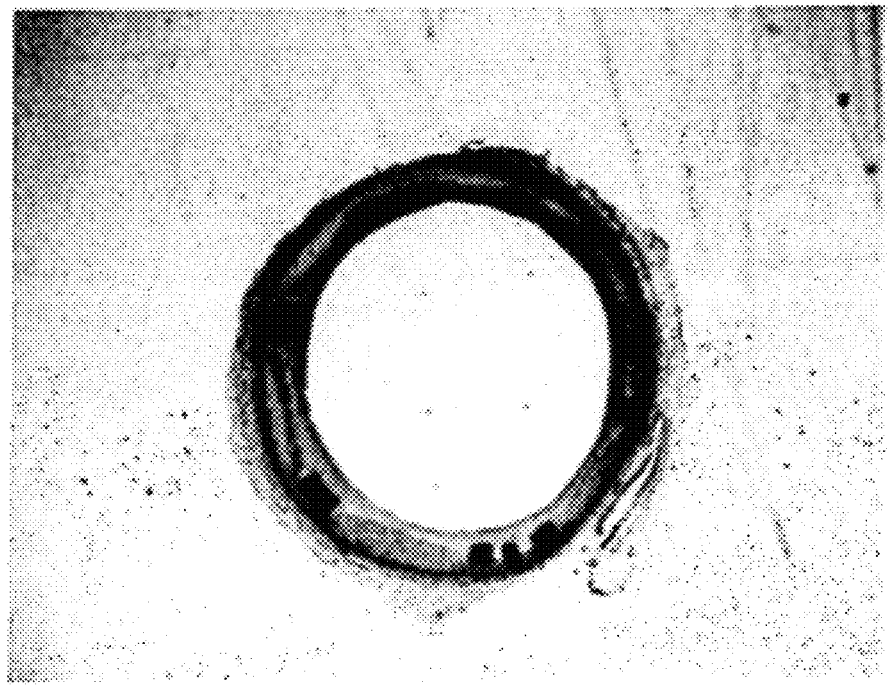
FIG. 7A

PRIMER COATING OF INORGANIC MATERIAL FOR IMPLANTABLE DEVICES

CROSS-REFERENCE

This is a divisional of U.S. patent application Ser. No. 10/751,289, filed Jan. 2, 2004 now U.S. Pat. No. 7,820,190 which is a continuation application of U.S. patent application Ser. No. 09/750,595, filed on Dec. 28, 2000 and issued on Sep. 14, 2004 as U.S. Pat. No. 6,790,228. U.S. patent application Ser. No. 10/751,289 was filed on Jan. 2, 2004, and issued as U.S. Pat. No. 7,820,190 on Oct. 26, 2010.

BACKGROUND OF THE INVENTION

1. Field of the Invention

The invention relates to coatings and methods of forming the coatings on implantable devices or endoluminal prostheses, such as stents.

2. Description of the Background

Percutaneous transluminal coronary angioplasty (PTCA) is a procedure for treating heart disease. A catheter assembly having a balloon portion is introduced percutaneously into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially press against the atherosclerotic plaque of the lesion for remodeling of the vessel wall. The balloon is then deflated to a smaller profile to allow the catheter to be withdrawn from the patient's vasculature.

A problem associated with the above procedure includes formation of intimal flaps or torn arterial linings which can collapse and occlude the conduit after the balloon is deflated. Vasospasms and recoil of the vessel wall also threaten vessel closure. Moreover, thrombosis and restenosis of the artery may develop over several months after the procedure, which may require another angioplasty procedure or a surgical by-pass operation. To reduce the partial or total occlusion of the artery by the collapse of arterial lining, and to reduce the chance of the development of thrombosis and restenosis, an expandable, intraluminal prosthesis, one example of which includes a stent, is implanted in the lumen to maintain the vascular patency.

Stents are used not only as a mechanical intervention but also as a vehicle for providing biological therapy. As a mechanical intervention, stents act as scaffoldings, functioning to physically hold open and, if desired, to expand the wall of the passageway. Typically stents are capable of being compressed, so that they can be inserted through small cavities via catheters, and then expanded to a larger diameter once they are at the desired location. Examples in the patent literature disclosing stents which have been successfully applied in PTCA procedures include stents illustrated in U.S. Pat. No. 4,733,665 issued to Palmaz, U.S. Pat. No. 4,800,882 issued to Gianturco, and U.S. Pat. No. 4,886,062 issued to Wiktor. Mechanical intervention via stents has reduced the rate of restenosis as compared to balloon angioplasty; but restenosis is still a significant clinical problem with rates ranging from 20-40%. When restenosis does occur in the stented segment, its treatment can be challenging, as clinical options are more limited as compared to lesions that were treated solely with a balloon.

Biological therapy can be achieved by medicating the stents. Medicated stents provide for the local administration of a therapeutic substance at the diseased site. In order to provide an efficacious concentration to the treated site, systemic administration of such medication often produces adverse or toxic side effects for the patient. Local delivery is a preferred method of treatment in that smaller total levels of medication are administered in comparison to systemic dosages, but are concentrated at a specific site. Local delivery thus produces fewer side effects and achieves more favorable results.

One proposed method for medicating stents disclosed seeding the stents with endothelial cells (Dichek, D. A. et al. Seeding of Intravascular Stents With Genetically Engineered Endothelial Cells; Circulation 1989; 80: 1347-1353). Briefly, endothelial cells were seeded onto stainless steel stents and grown until the stents were covered. The cells were therefore able to be delivered to the vascular wall where they provided therapeutic proteins. Another proposed method of providing a therapeutic substance to the vascular wall included use of a heparin-coated metallic stent, whereby a heparin coating was ionically or covalently bonded to the stent. Significant disadvantages associated with the aforementioned method includes significant loss of the therapeutic substance from the body of the stent during delivery and expansion of the stent, an absolute lack of control of the release rate of the proteins from the stent, and the inherent limitation as to the type of therapeutic substance that can be used.

Another proposed method involved the use of a polymeric carrier coated onto the surface of a stent, as disclosed in U.S. Pat. No. 5,464,650 issued to Berg et al. Berg disclosed applying to a stent body a solution which included a specified solvent, a specified polymer dissolved in the solvent, and a therapeutic substance dispersed in the blend. The solvent was allowed to evaporate, leaving on the stent surface a coating of the polymer and the therapeutic substance impregnated in the polymer. Among the specified, suitable choices of polymers listed by Berg, empirical results were specifically provided for poly(caprolactone) and poly(L-lactic acid). The preferred choice of mutually compatible solvents included acetone or chloroform. As indicated in Berg, stents where immersed in the solution 12 to 15 times or sprayed 20 times. The evaporation of the solvent provided a white coating. A white coloration is generally indicative of a brittle coating. A brittle coating is an undesirable characteristic, since portions of the coating typically become detached during stent expansion. Detachment of the coating causes the quantity of the therapeutic substance to fall below a threshold level sufficient for the effective treatment of a patient.

It is desirable to improve the adhesion or retention of the polymeric coating to the surface of a prosthesis, e.g., stent. It is also desirable to be able to increase the quantity of the therapeutic substance carried by the polymeric layer without perturbing the mechanical properties of the coating, such as inadequate coating adhesion, or significantly increasing the thickness of the coating.

It is additionally desirable to provide an improved polymeric coating that is susceptible to delivery and expansion with a prosthesis without significant detachment from the surface of the prosthesis. An improved polymeric coating is also needed which allows for a significant control of the release of the therapeutic substance.

It may also be advantageous to maintain the concentration of the therapeutic substance at a therapeutically acceptable level for a prolonged duration of time. Depending on the physiological mechanism targeted, the therapeutic substance may be required to be released at the target site for an extended duration of time. Accordingly, it is desirable to provide a coating which can maintain the residence time of a substance at a therapeutically useful concentration for an effective duration of time.

SUMMARY OF THE INVENTION

In accordance with one aspect of the present invention, a prosthesis is provided, such as a balloon-expandable stent or a self-expandable stent, which includes a coating having a reservoir region carrying an active ingredient, e.g., actinomycin D or taxol. A primer region, free from any active ingredients, can be disposed between the reservoir region and the surface of the prosthesis. The primer can act as an intermediary tie layer between the surface of the prosthesis and the reservoir region. The primer and reservoir regions can be made form the same polymeric material or different polymeric materials. The prosthesis can additionally include a barrier region disposed on a selected portion of the reservoir region for reducing the rate at which the active ingredient is released. In one embodiment, the barrier layer contains inorganic particles. Examples of suitable polymeric materials for the primer layer include polyisocyanates, unsaturated polymers, amine content polymers, acrylates, polymers containing a high content of hydrogen bonding groups, and inorganic polymers. Biocompatible polymers can be used not only for the primer region, but also for the reservoir region. One examples of a biocompatible polymer includes ethylene vinyl alcohol copolymer.

In accordance with another aspect of the present invention, a method is provided for forming a coating for an implantable device comprising forming a primer on at lease a selected portion of a surface of the implantable device and forming a reservoir region containing an active ingredient on at least a selected portion of the primer. The primer can provide an adhesive tie layer between the surface of the implantable device and the reservoir region. In one embodiment, the method can additionally include forming a barrier layer on at lease a selected portion of the reservoir region for reducing the rate at which the active ingredient is released from the reservoir region.

In one embodiment, the act of forming the primer comprises applying a composition to a selected portion of the surface of the implantable device wherein the composition includes a thermoplastic polymer added to a solvent, and heating the composition applied to the implantable device to a temperature greater than about the glass transition temperature and less than about the melting temperature of the polymer.

In accordance with another embodiment, the act of forming the primer comprises applying a composition to a selected portion of the surface of the implantable device, wherein the composition comprises an inorganic polymer added to a solvent, and significantly removing the solvent to form the primer.

In accordance with another embodiment, the act of forming the primer comprises applying a composition to a selected portion of the surface of the implantable device, wherein the composition comprises a polymer added to a solvent, and heating the composition applied to the selected portion of the surface of the implantable device to a temperature above the glass transition temperature of the polymer.

In accordance with another embodiment, the act of forming the primer comprises applying a composition to a selected portion of the surface of the implantable device, wherein the composition comprises a prepolymer and an initiator, e.g., a free radical or UV initiator. The composition is then exposed to a condition such as UV radiation or heat to polymerize the prepolymer.

In accordance with another aspect of the present invention, a coating for a stent is provided containing a first active ingredient and a second active ingredient, wherein the rate of release of the first active ingredient is slower than the rate of release of the second active ingredient. The coating can be made from a polymeric material such as an ethylene vinyl alcohol copolymer. The coating can include a first region containing the first and second active ingredients, and a second region, free from any active ingredients, located between the first region and the surface of the stent. The second region increases the ability of the coating to be retained by the stent.

BRIEF DESCRIPTION OF THE FIGURE

FIG. 6A is a picture of a histology slide of a coronary vessel from the control group in accordance with Example 16;

FIG. 6B is a picture of a histology slide of a coronary vessel from the actinomycin D group in accordance with Example 16

FIG. 7A is a picture of a histology slide of a coronary vessel from the control group in accordance with Example 26.

DETAILED DESCRIPTION OF THE EMBODIMENTS

Composition for Forming the Primer Layer

Figure 1A:
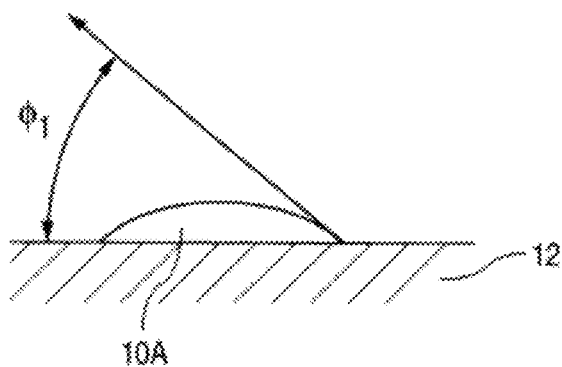
FIG. 1A illustrates a fluid on a solid substrate having a contact angle $\Phi_1$.

The embodiments of the composition for a primer layer are prepared by conventional methods wherein all components are combined, then blended. More particularly, in accordance to one embodiment, a predetermined amount of a polymer or a prepolymer is added to a predetermined amount of a solvent or a combination of solvents. The mixture can be prepared in ambient pressure and under anhydrous atmosphere. If necessary, a free radical or UV initiator can be added to the composition for initiating the curing or cross-linking of the prepolymer. Heating and stirring and/or mixing can be employed to effect dissolution of the polymer into the solvent.

"Polymer," "poly," and "polymeric" are defined as compounds that are the product of a polymerization reaction and are inclusive of homopolymers, copolymers, terpolymers etc., including random, alternating, block, and graft variations thereof. The polymers should have a high capacity of adherence to the surface of an implantable device, such as a metallic surface of a stent. Stainless steel, such as 316L, is a commonly used material for the manufacturing of a stent.

Stainless steel includes a chromium oxide surface layer which makes the stent corrosion resistant and confers, in large part, biocompatibility properties to the stent. The chromium oxide layer presents oxide, anionic groups, and hydroxyl moieties, which are polar. Consequently, polymeric materials with polar substituents and cationic groups can adhere to the surface. Representative examples of suitable polymeric material include polyisocyanates, unsaturated polymers, high amine content polymers, acrylates, polymers with high content of hydrogen bonding groups, silane coupling agents, titanates and zirconates.

Representative examples of polyisocyanates include triisocyanurate, alphatic polyisocyanate resins based on hexamethylene diisocyanate, aromatic polyisocyanate prepolymers based on diphenylmethane diisocyanate, polyisocyanate polyether polyurethanes based on diphenylmethane diisocyanate, polymeric isocyanates based on toluene diisocyanate, polymethylene polyphenyl isocyanate, and polyester polyurethanes.

Representative examples of unsaturated polymers include polyester diacrylates, polycaprolactone diacrylates, polyester diacrylates, polytetramethylene glycol diacrylate, polyacrylates with at least two acrylate groups, polyacrylated polyurethanes, and triacrylates. With the use of unsaturated prepolymers a free radical or UV initiator can be added to the composition for the thermal or UV curing or cross-linking process. For thermal curing, examples of free radicals initiators are benzoyl peroxide; bis(2,4-dichlorobenzoyl) peroxide; dicumyl peroxide; 2,5-bis(tert-butyl peroxy)-2,5-dimethyl hexane; ammonium persulfate, and 2,2'-azobisisobutyronitrile. As is understood by one of ordinary skill in the art, each initiator requires a different temperature to induce decomposition. For UV curing, examples of initiators include 2,2-dimethoxy-2-phenylacetophenone; 1-hydroxycyclohexyl phenyl ketone; benzoin ethyl ether; and benzophenone. These initators can be activated by illumination with a medium pressure Hg bulb that contains wavelengths between 250 and 350 nm.

Representative examples of high amine content polymers include polyethyleneamine, polyallylamine, and polylysine.

Representative examples of acrylates include copolymers of ethyl acrylate, methyl acrylate, butyl methacrylate, methacrylic acid, acrylic acid, and cyanoacrylates.

Representative examples of high content of hydrogen bonding group polymers include polyethylene-co-polyvinyl alcohol, epoxy polymers based on the diglycidylether of bisphenol A with amine crosslinking agents, epoxy polymers cured by polyols and lewis acid catalysts, epoxy phenolics, epoxy-polysulfides, ethylene vinyl acetate, melamine formaldehydes, polyvinylalcohol-co-vinyl acetate polymers, resorcinol-formaldehydes, urea-formaldehydes, polyvinylbutyral, polyvinylacetate, alkyd polyester resins, acrylic acid modified ethylene vinyl acetate polymers, methacrylic acid modified ethylene vinyl acetate polymers, acrylic acid modified ethylene acrylate polymers, methacrylic acid modified ethylene acrylate polymers, anhydride modified ethylene acrylate copolymers, and anhydride modified ethylene vinyl acetate polymers.

Representative examples of silane coupling agents include 3-aminopropyltriethoxysilane and (3-glycidoxypropyl)methyldiethoxysilane.

Representative examples of titanates include tetra-iso-propyl titanate and tetra-n-butyl titanate.

Representative examples of zirconates include n-propyl zirconate and n-butyl zirconate.

Biocompatible polymers can also be used for the primer material. Examples of biocompatible primers include poly (hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydrides, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonates), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. Also, polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Ethylene vinyl alcohol is functionally a very suitable choice of polymer. Ethylene vinyl alcohol copolymer, commonly known by the generic name EVOH or by the trade name EVOH, refers to copolymers comprising residues of both ethylene and vinyl alcohol monomers. One of ordinary skill in the art understands that ethylene vinyl alcohol copolymer may also be a terpolymer so as to include small amounts of additional monomers, for example less than about five (5) mole percentage of styrenes, propylene, or other suitable monomers. In a useful embodiment, the copolymer comprises a mole percent of ethylene of from about 27% to about 47%. Typically, 44 mole percent ethylene is suitable. Ethylene vinyl alcohol copolymers are available commercially from companies such as Aldrich Chemical Company, Milwaukee, Wis., or EVOH Company of America, Lisle, Ill., or can be prepared by conventional polymerization procedures that are well known to one of ordinary skill in the art. The copolymer possesses good adhesive qualities to the surface of a stent, particularly stainless steel surfaces, and has illustrated the ability to expand with a stent without any significant detachment of the copolymer from the surface of the stent.

The solvent should be mutually compatible with the polymer and should be capable of placing the polymer into solution at the concentration desired in the solution. Useful solvents should also be able to expand the chains of the polymer for maximum interaction with the surface of the device, such as a metallic surface of a stent. Examples of solvent can include, but are not limited to, dimethylsulfoxide (DMSO), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures thereof.

By way of example, and not limitation, the polymer can comprise from about 0.1% to about 35%, more narrowly about 2% to about 20% by weight of the total weight of the composition, and the solvent can comprise from about 65% to about 99.9%, more narrowly about 80% to about 98% by weight of the total weight of the composition. A specific weight ratio is dependent on factors such as the material from which the implantable device is made and the geometrical structure of the device.

Figure 1B:
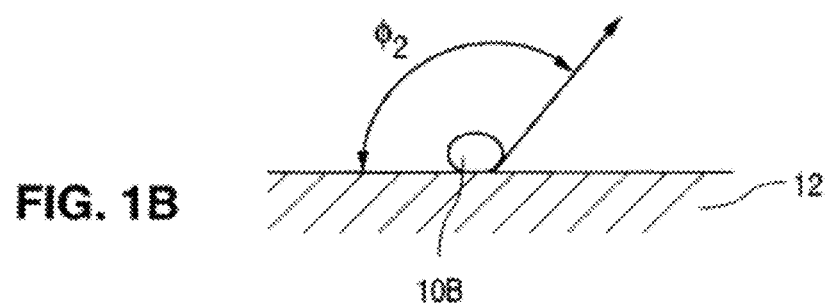
FIG. 1B illustrates a fluid on a solid substrate having a contact angle $\Phi_2$.

In accordance with another embodiment, a fluid can be added to the composition to enhance the wetting of the composition for a more uniform coating application. To enhance the wetting of the composition, a suitable fluid typically has a high capillary permeation. Capillary permeation or wetting is the movement of a fluid on a solid substrate driven by interfacial energetics. Capillary permeation is quantitated by a contact angle, defined as an angle at the tangent of a droplet in a fluid phase that has taken an equilibrium shape on a solid surface. A low contact angle means a higher wetting liquid. A suitably high capillary permeation corresponds to a contact angle less than about 90°. FIG. 1A illustrates a fluid droplet 10A on a solid substrate 12, for example a stainless steel surface. Fluid droplet 10A has a high capillary permeation that corresponds to a contact angle $\Phi_1$, which is less than about 90°. In contrast, FIG. 1B illustrates a fluid droplet 10B on solid substrate 12, having a low capillary permeation that corresponds to a contact angle $\Phi_2$, which is greater than about 90°. The wetting fluid, typically, should have a viscosity not greater than about 50 centipoise, narrowly about 0.3 to about 5 centipoise, more narrowly about 0.4 to about 2.5 centipoise. The wetting fluid, accordingly, when added to the composition, reduces the viscosity of composition.

The wetting fluid should be mutually compatible with the polymer and the solvent and should not precipitate the polymer. The wetting fluid can also act as the solvent. Useful examples of the wetting fluid include, but are not limited to, tetrahydrofuran (THF), dimethylformamide (DMF), 1-butanol, n-butyl acetate, dimethyl acetamide (DMAC), and mixtures and combinations thereof. By way of example and not limitation, the polymer can comprise from about 0.1% to about 35%, more narrowly from about 2% to about 20% by weight of the total weight of the composition; the solvent can comprise from about 19.9% to about 98.9%, more narrowly from about 58% to about 84% by weight of the total weight of the composition; the wetting fluid can comprise from about 1% to about 80%, more narrowly from about 5% to about 40% by weight of the total weight of the composition. The specific weight ratio of the wetting fluid depends on the type of wetting fluid employed and type of and the weight ratio of the polymer and the solvent. More particularly, tetrahydrofuran used as the wetting fluid can comprise, for example, from about 1% to about 44%, more narrowly about 21% by weight of the total weight of the solution. Dimethylformamide used as the wetting fluid can comprise, for example, from about 1% to about 80%, more narrowly about 8% by weight of the total weight of the solution. 1-butanol used as the wetting fluid can comprise, for example, from about 1% to about 33%, more narrowly about 9% by weight of the total weight of the solution. N-butyl acetate used as the wetting fluid can comprise, for example, from about 1% to about 34%, more narrowly about 14% by weight of the total weight of the solution. Dimethyl acetamide used as the wetting fluid can comprise, for example, from about 1% to about 40%, more narrowly about 20% by weight of the total weight of the solution.

The presence of an active ingredient in a polymeric matrix typically interferes with the ability of the matrix to adhere effectively to the surface of the device. An increase in the quantity of the active ingredient reduces the effectiveness of the adhesion. High drug loadings of, for example, 10-40% by weight in the coating significantly hinder the retention of the coating on the surface of the device. The primer layer serves as a functionally useful intermediary layer between the surface of the device and an active ingredient-containing or reservoir coating. The primer layer provides for an adhesive tie between the reservoir coating and the device—which, in effect, would also allow for the quantity of the active ingredient in the reservoir coating to be increased without compromising the ability of the reservoir coating to be effectively contained on the device during delivery and, if applicable, expansion of the device. Ethylene vinyl alcohol copolymer adheres well to metallic surfaces, particularly devices made from stainless steel. The copolymer has illustrated good elastic qualities, which allow the copolymer to be delivered and, if applicable, expanded with the device without any significant detachment of the copolymer form the surface of the device.

Table 1 illustrates some examples of suitable combinations for the primer composition:

TABLE 1

| Polymer | Solvent | Wetting Fluid | Initiators |
| --- | --- | --- | --- |
| EVOH | DMSO | — | — |
| EVOH | DMSO | THF | — |
| polyester polyurethanes | dimethylformamide | — | — |
| polyester polyurethanes | dimethylformamide | DMAC | — |
| polycaprolactone | chloroform | n-butyl acetate | — |
| polyacrylate polyurethane | ethyl acetate | — | benzophenone |
| polyacrylated polyurethane | ethyl acetate | — | 1-hydroxycyclohexyl phenyl ketone |
| polyethyleneamine | $H_2O$ | — | — |
| methacrylic acid copolymer | THF | — | — |
| ethylene vinylacetate (e.g., 40% vinyl acetate content) | methylethylketone | — | — |
| aminopropyltriethoxysilane | ethanol/water 95/5 blend (w/w) | — | — |
| (3-glydidoxypropyl) methyldiethoxysilane | toluene | — | — |
| tetra-iso-propyl titanate (e.g., 0.25% w/w in isopropanol) | isopropanol | — | — |
| tetra-n-butyl titanate (e.g., 0.1-5% w/w in ethyl acetate) | ethyl acetate | — | — |

Composition for Forming the Active Ingredient Layer

The embodiments of the composition for an active ingredient-containing or reservoir layer are prepared by conventional methods wherein all components are combined, then blended. More particularly, in accordance to one embodiment, a predetermined amount of a polymeric compound is added to a predetermined amount of a mutually compatible solvent or combination of solvents. The polymeric compound can be added at ambient pressure and under anhydrous atmosphere. If necessary, gentle heating and stirring and/or mixing can be employed to effect dissolution of the polymer into the solvent, for example 12 hours in a water bath at about 60° C.

The polymer chosen must be a polymer that is biocompatible and minimizes irritation to the vessel wall when the device is implanted. The polymer may be either a biostable or a bioabsorbable polymer. Bioabsorbable polymers that could be used include poly(hydroxyvalerate), poly(L-lactic acid), polycaprolactone, poly(lactide-co-glycolide), poly(hydroxybutyrate), poly(hydroxybutyrate-co-valerate), polydioxanone, polyorthoesters, polyanhydrides, poly(glycolic acid), poly(D,L-lactic acid), poly(glycolic acid-co-trimethylene carbonate), polyphosphoesters, polyphosphoester urethanes, poly(amino acids), cyanoacrylates, poly(trimethylene carbonate), poly(iminocarbonate), copoly(ether-esters) (e.g. PEO/PLA), polyalkylene oxalates, polyphosphazenes and biomolecules such as fibrin, fibrinogen, cellulose, starch, collagen and hyaluronic acid. Also, biostable polymers with a relatively low chronic tissue response such as polyurethanes, silicones, and polyesters could be used and other polymers could also be used if they can be dissolved and cured or polymerized on the stent such as polyolefins, polyisobutylene and ethylene-alphaolefin copolymers; acrylic polymers and copolymers, vinyl halide polymers and copolymers, such as polyvinyl chloride; polyvinyl ethers, such as polyvinyl methyl ether; polyvinylidene halides, such as polyvinylidene fluoride and polyvinylidene chloride; polyacrylonitrile; polyvinyl ketones; polyvinyl aromatics, such as polystyrene; polyvinyl esters, such as polyvinyl acetate; copolymers of vinyl monomers with each other and olefins, such as ethylene-methyl methacrylate copolymers, acrylonitrile-styrene copolymers, ABS resins, and ethylene-vinyl acetate copolymers; polyamides, such as Nylon 66 and polycaprolactam; alkyd resins; polycarbonates; polyoxymethylenes; polyimides; polyethers; epoxy resins; rayon; rayon-triacetate; cellulose, cellulose acetate, cellulose butyrate; cellulose acetate butyrate; cellophane; cellulose nitrate; cellulose propionate; cellulose ethers; and carboxymethyl cellulose.

Ethylene vinyl alcohol is functionally a very suitable choice of polymer. The copolymer allows for good control capabilities over the release rate of the active ingredient. As a general rule, an increase in the amount of the ethylene comonomer content decreases the rate that the active ingredient is released from the copolymer matrix. The release rate of the active ingredient typically decreases as the hydrophilicity of the copolymer decreases. An increase in the amount of the ethylene comonomer content increases the overall hydrophobicity of the copolymer, especially as the content of vinyl alcohol is concomitantly reduced. It is also known that the release rate and the cumulative amount of the active ingredient that is released is directly proportional to the total initial content of the ingredient in the copolymer matrix. Accordingly, a wide spectrum of release rates can be achieved by modifying the ethylene comonomer content and the initial amount of the active ingredient.

The choice of polymer for the reservoir layer can be the same as or different from the selected polymer for the primer layer. The use of the same polymer significantly reduces or eliminates any interfacial incompatibilities, such as lack of an adhesive tie or bond, which may exist with the employment of two different polymeric layers. In effect, it can be said that the use of the same polymeric material for the primer layer and the reservoir layer results in the formation of a single-layered coating.

The solvent should be capable of placing the polymer into solution at the concentration desired in the solution. Examples of solvent can include, but are not limited to, DMSO, chloroform, acetone, water (buffered saline), xylene, acetone, methanol, ethanol, 1-propanol, tetrahydrofuran, 1-butanone, dimethylformamide, dimethylacetamide, cyclohexanone, and N-methylpyrrolidinone. With the use of low ethylene content, e.g., 29 mol %, ethylene vinyl alcohol copolymer, a suitable choice of solvent is iso-propylalcohol (IPA) admixed with water.

Sufficient amounts of an active ingredient are dispersed in the blended composition of the polymer and the solvent. The active ingredient should be in true solution or saturated in the blended composition. If the active ingredient is not completely soluble in the composition, operations including mixing, stirring, and/or agitation can be employed to effect homogeneity of the residues. The active ingredient may be added so that the dispersion is in fine particles. The mixing of the active ingredient can be conducted in an anhydrous atmosphere, at ambient pressure, and at room temperature such that supersaturating the active ingredient is not desired.

The active ingredient should inhibit the activity of vascular smooth muscle cells. More specifically, the active ingredient is aimed at inhibiting abnormal or inappropriate migration and/or proliferation of smooth muscle cells.

"Smooth muscle cells" include those cells derived from the medial and adventitial layers of the vessel which proliferate in intimal hyperplastic vascular sites following vascular trauma or injury. Under light microscopic examination, characteristics of smooth muscle cells include a histological morphology of a spindle shape with an oblong nucleus located centrally in the cell with nucleoli present and myofibrils in the sarcoplasm. Under electron microscopic examination, smooth muscle cells have long slender mitochondria in the juxtanuclear sarcoplasm, a few tubular elements of granular endoplasmic reticulum, and numerous clusters of free ribosomes. A small Golgi complex may also be located near one pole of the nucleus.

"Migration" of smooth muscle cells means movement of these cells in vivo from the medial layers of a vessel into the intima, such as may also be studied in vitro by following the motion of a cell from one location to another, e.g., using time-lapse cinematography or a video recorder and manual counting of smooth muscle cell migration out of a defined area in the tissue culture over time.

"Proliferation" of smooth muscle cells means increase in cell number.

"Abnormal" or "inappropriate" proliferation means division, growth or migration of cells occurring more rapidly or to a significantly greater extent than typically occurs in a normally functioning cell of the same type, i.e., hyper-proliferation.

"Inhibiting" cellular activity means reducing, delaying or eliminating smooth muscle cell hyperplasia, restenosis, and vascular occlusions, particularly following biologically or mechanically mediated vascular injury or trauma or under conditions that would predispose a mammal to suffer such a vascular injury or trauma. As used herein, the term "reducing"

means decreasing the intimal thickening that results from stimulation of smooth muscle cell proliferation. "Delaying" means retarding the progression of the hyper-proliferative vascular disease or delaying the time until onset of visible intimal hyperplasia, as observed, for example, by histological or angiographic examination. "Elimination" of restenosis following vascular trauma or injury means completely "reducing" and/or completely "delaying" intimal hyperplasia in a patient to an extent which makes it no longer necessary to surgically intervene, i.e., to re-establish a suitable blood flow through the vessel by, for example, repeat angioplasty, atherectomy, or coronary artery bypass surgery. The effects of reducing, delaying, or eliminating restenosis may be determined by methods known to one of ordinary skill in the art, including, but not limited to, angiography, intravascular ultrasound, fluoroscopic imaging, fiber optic visualization, optical coherence tomography, intravascular MRI, or biopsy and histology. Biologically mediated vascular injury includes, but is not limited to, injury caused by or attributed to autoimmune disorders, alloimmune related disorders, infectious disorders including endotoxins and herpes viruses such as cytomegalovirus, metabolic disorders such as atherosclerosis, and vascular injury resulting from hypothermia and irradiation. Mechanically mediated vascular injury includes, but is not limited to, vascular injury caused by catheterization procedures or vascular scraping procedures such as percutaneous transluminal coronary angioplasty, vascular surgery, stent placement, transplantation surgery, laser treatment, and other invasive procedures which disrupted the integrity of the vascular intima or endothelium. The active ingredient of the invention is not restricted in use for therapy following vascular injury or trauma; rather, the usefulness of the active ingredient will also be determined by the ingredient's ability to inhibit cellular activity of smooth muscle cells or inhibit the development of restenosis.

The active ingredient also includes any substance capable of exerting a therapeutic or prophylactic effect in the practice of the present invention as well as having positive pharmacological effects on the expression of the extracellular matrix. The active ingredient can also be for enhancing wound healing in a vascular site and improving the structural and elastic properties of the vascular site. Examples of such active ingredients include antiproliferative substances as well as antineoplastic, antiinflammatory, antiplatelet, anticoagulant, antifibrin, antithrombin, antimitotic, antibiotic, antioxidant, and combinations thereof. A suitable example of an antiproliferative substance includes actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. Examples of suitable antineoplastics include paclitaxel and docetaxel. Examples of suitable antiplatelets, anticoagulants, antifibrins, and antithrombins include sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen), and 7E-3B® (an antiplatelet drug from Centocore). Examples of suitable antimitotic agents include methotrexate, azathioprine, vincristine, vinblastine, fluorouracil, adriamycin, and mutamycin. Examples of suitable cytostatic or antiproliferative agents include angiopeptin (a somatostatin analog from Ibsen), angiotensin converting enzyme inhibitors such as CAPTOPRIL (available from Squibb), CILAZAPRIL (available from Hoffman-LaRoche), or LISINOPRIL (available from Merck); calcium channel blockers (such as Nifedipine), colchicine, fibroblast growth factor (FGF) antagonists, fish oil (omega 3-fatty acid), histamine antagonist, LOVASTATIN (an inhibitor of HMG-CoA reductase, a cholesterol lowering drug from Merck), monoclonal antibodies (such as PDGF receptors), nitroprusside, phosphodiesterase inhibitors, prostaglandin inhibitor (available form Glazo), Seramin (a PDGF antagonist), serotonin blockers, steroids, thioprotease inhibitors, triazolopyrimidine (a PDGF antagonist), and nitric oxide. Other therapeutic substances or agents which may be appropriate include alpha-interferon, genetically engineered epithelial cells, and dexamethasone. Exposure of the composition to the active ingredient is not permitted to adversely alter the active ingredient's composition or characteristic. Accordingly, the particular active ingredient is selected for mutual compatibility with the blended composition.

The dosage or concentration of the active ingredient required to produce a favorable therapeutic effect should be less than the level at which the active ingredient produces toxic effects and greater than the level at which non-therapeutic results are obtained. The dosage or concentration of the active ingredient required to inhibit the desired cellular activity of the vascular region can depend upon factors such as the particular circumstances of the patient; the nature of the trauma; the nature of the therapy desired; the time over which the ingredient administered resides at the vascular site; and if other bioactive substances are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

By way of example, the polymer can comprise from about 0.1% to about 35%, more narrowly from about 2% to about 20% by weight of the total weight of the composition, the solvent can comprise from about 59.9% to about 99.8%, more narrowly from about 79% to about 87% by weight of the total weight of the composition, and the active ingredient can comprise from about 0.1% to about 40%, more narrowly from about 1% to about 9% by weight of the total weight of the composition. More than 9% by weight of the active ingredient could adversely affect characteristics that are desirable in the polymeric coating, such as adhesion of the coating to the device. With the use of the primer layer, weight ratios of more than 9% for the active ingredient are achievable. Selection of a specific weight ratio of the polymer and solvent is dependent on factors such as, but not limited to, the material from which the device is made, the geometrical structure of the device, and the type and amount of the active ingredient employed. The particular weight percentage of the active ingredient mixed within the composition depends on factors such as duration of the release, cumulative amount of release, and release rate that is desired.

Optionally, a second fluid or solvent, such as tetrahydrofuran (THF) or dimethylformamide (DMF) can be used to improve the solubility of an active ingredient in the composition and/or to increase the wetting of the composition. Increasing the wetting of the composition has been discovered to lead to the application of a more uniformed coating. The second fluid or solvent can be added to the composition or the active ingredient can be added to the second solvent prior to admixture with the blend.

In this embodiment with a second fluid, by way of example, the polymer can comprise from about 0.1% to about 35%, more narrowly from about 2% to about 20% by weight of the total weight of the composition, the solvent can comprise from about 19.8% to about 98.8%, more narrowly from about 49% to about 79% by weight of the total weight of the composition, the second solvent can comprise from about 1% to about 80%, more narrowly from about 5% to about 40% by weight of the total weight of the composition, and the active ingredient can comprise from about 0.1% to about 40%, more narrowly from about 1% to about 9% by weight of the total weight of the composition. Selection of a specific weight ratio of the polymer, the solvent, and the second solvent is dependent on factors such as, but not limited to, the material from which the implantable device is made, the geometrical structure of the device, and the type and amount of the active ingredient employed. The particular weight percentage of the active ingredient mixed within the composition depends on factors such as duration of the release, cumulative amount of release, and release rate that is desired.

Table 2 is an exemplary list of suitable combinations in accordance with various embodiment of the present invention:

TABLE 2

| POLYMER | SOLVENT | SECOND SOLVENT | ACTIVE INGREDIENT |
|---|---|---|---|
| EVOH (29 mol % ethylene content e.g., Soarnol ®) | IPA/H$_2$O (1:1) | — | Actinomycin D |
| EVOH (44 mol % ethylene content) | DMSO | THF | Actinomycin D |
| EVOH | DMSO | THF | Actinomycin D |
| EVOH | DMSO | DMF | Paclitaxel |
| poly(L-lactic acid) | chloroform | — | dexamethasone |
| poly(lactic acid-co-glycolic acid) | acetone | — | dexamethasone |
| Polyether urethane | N-methyl pyrrolidinone | — | tocopherol |

Composition for Forming the Rate Reducing Membrane

The embodiments of the composition for a rate-reducing membrane or diffusion barrier layer are prepared by conventional methods wherein all components are combined. In the embodiment with the use of particles, dispersion techniques should also be employed to circumvent agglomeration or formation of particle flocs.

More particularly, in accordance with one embodiment, the embodiments for the composition for the reservoir layer can be applied on a selected region of the reservoir layer to form a rate reducing member or a barrier layer. The barrier layer can reduce the rate of release or delay the time at which the active ingredient is released from the reservoir layer. In one embodiment, for maximum blood compatibility, polyethylene glycol or polyethylene oxide can also be added to the blend. Ethylene vinyl alcohol is functionally a very suitable choice of polymer. The copolymer allows for good control capabilities over the release rate of the active ingredient. As a general rule, an increase in the amount of the ethylene comonomer content decreases the rate that the active ingredient is released from the copolymer matrix. The release rate of the active ingredient decreases as the hydrophilicity of the polymer decreases. An increase in the amount of the ethylene comonomer content increases the overall hydrophobicity of the copolymer, especially as the content of vinyl alcohol is concomitantly reduced.

Usefully, the choice of polymer for the barrier layer can be the same as the selected polymer for the reservoir. The use of the same polymer, as described for some of the embodiments, significantly reduces or eliminates any interfacial incompatibilities, such as lack of adhesion, which may exist in the employment of two different polymeric layers. In effect, it can be said that the use, if desired, of the same polymeric material for the barrier layer and the reservoir layer results in the formation of a single-layered coating. In other words, the use of the same polymeric material results in a seamless multi-layered coating in which the layers vary in terms of their content. Defined interfacial boundaries are, accordingly, significantly reduced or eliminated.

In accordance with another embodiment, particles of inorganic or organic type are added to the blend. The particles should be dispersed in the blend. Dispersed is defined as the particles being present as individual particles, not agglomerates or flocs. In certain polymer-solvent blends, certain particles will disperse with ordinary mixing. Otherwise the particles can be dispersed in the composition by high shear processes such as ball mill, disc mill, sand mill, attritor, rotor stator mixer, ultrasonication—all such high shear dispersion techniques being well known to one of ordinary skill in the art. Optionally, one of the aforementioned wetting fluids can also be added to the blend. The wetting fluid can be added prior to, contemporaneously with, or subsequent to the agitation. Biocompatible dispersing agents in the form of surfactants, emulsifiers, or stabilizers may also be added to the blend to assist in particle dispersion.

The particles can be made from any suitable material having barrier-type properties, such as, but not limited to tortuousity, excluded volume, and adsorptivity. Tortuosity refers to the exclusion of space in the polymer matrix for the creation of a defined space or a tortuous path through and about which the active ingredient must travel to be expelled from the layer. Excluded volume refers to the volume displaced by the particles that would otherwise be available for the diffusion of the active ingredient. Adsorptivity refers to the chromatographic effect which is dependent upon the interaction between the active ingredient used in combination with the particle. The active ingredient may be partially adsorbed and released by the surface of the particles, such as silica or fumed carbon particles.

In one embodiment, the particles can be made from a metal oxide, such as rutile titanium oxide, anatase titanium dioxide, niobium oxide, tantalum oxide, zirconium oxide, iridium oxide, or tungsten oxide. In another embodiment, the particles can be made from a main group oxide such as silica (silicon oxide) or alumina (aluminum oxide). Metallic particles such as gold, hafnium, platinum, iridium, palladium, tungsten, tantalum, niobium, zirconium, titanium, aluminum, or chromium can also be employed. In another embodiment, carbonaceous particles made from, for example, lamp black, furnace black, carbon black, fumed carbon black, gas black, channel black, activated charcoal, diamond, diamond like carbon, or CVD diamond can be employed. In yet another embodiment, the particles can be made from nitrides such as titanium nitride, chromium nitride, and zirconium nitride. In yet another embodiment, carbides such as tungsten carbide, silicon carbide, or titanium carbide, and calcium salts such as hydroxyapatite, dahlite, brushite, tricalcium phosphate, calcium sulphate, and calcium carbonate can be used. Other inorganic particles can include particles made from silicides, barium titanate, and strontium titanate.

In yet another embodiment, the particles can be made from a suitable polymer including polymers of polyolefins, polyurethanes, cellulosics (i.e., polymers having mer units derived from cellulose), polyesters, polyamides, poly(hexamethylene isophthalamide/terephthalamide) (commercially available as SELAR PA™), poly(ethylene terephthalate-co-p-oxybenzoate) (PET/PHB, e.g., copolymer having about 60-80 mole percent PHB), poly(hydroxy amide ethers), polyacrylates, polyacrylonitrile, acrylonitrile/styrene copolymer (commercially available as LOPAC), rubber-modified acrylonitrile/acrylate copolymer (commercially available as BAREX), poly(methyl methacrylate), liquid crystal polymers (LCP) (e.g., VECTRA available from Hoescht-Celanese, ZENITE available from DuPont, and XYDAR available from Amoco Performance Chemicals), poly(phenylene sulfide), polystyrenes, polycarbonates, poly(vinyl alcohols), poly(ethylene-vinyl alcohol) (EVOH, e.g., having about 27 to about 47 mole percent of ethylene content), epoxies composed of bisphenol A based diepoxides with amine cure, aliphatic polyketones (e.g., CARILON available from Shell, and KETONEX available from British Petroleum), polysulfones, poly(ester-sulfone), polyurethane-sulfone), poly(carbonate-sulfone), poly(3-hydroxyoxetane), poly(amino ethers), gelatin, amylose, parylene-C, parylene-D, parylene-N.

Representatives polyolefins include those based upon alpha-monoolefin monomers having from about 2 to 6 carbon atoms and halogen substituted olefins, i.e., halogenated polyolefins. By way of example, and not limitation, low to high density polyethylenes, essentially unplasticized poly (vinyl chloride), poly (vinylidene chloride), poly (vinyl fluoride), poly (vinylidene fluoride), poly (tetrafluoroethylene) (Teflon), poly (chlorotrifluoroethylene) (KEL-F), and mixtures thereof are suitable. Low to high density polyethylenes are generally understood to have densities of about 0.92 g cm$^{-3}$ to about 0.96 g cm$^{-3}$, however, no bright line can be drawn for density classifications and the density can vary according to the supplier.

Representative polyurethanes include polyurethanes having a glass transition temperature above a storage or ambient temperature, for example having a glass transition temperature of at least 40° C. to 60° C., or having a non-polar soft segment which includes a hydrocarbon, silicone, fluorosilicone, or mixtures thereof. For example, ELAST-EON, manufactured by Elastomedic/CSIRO Molecular Science, is a polyurethane with a non-polar soft segment which is made from 1,4-butanediol, 4,4'-methylenediphenyl diisocyanate, and a soft segment composed of a blend poly(hexamethylene oxide) (PHMO) and bishydroxyethoxypropylpolydimethylsiloxane (PDMS). A useful example has a blend of 20% by weight PHMO and 80% by weight PDMS.

Representative examples of cellulosics include, but are not limited to, cellulose acetate having a degree of substitution (DS) greater than about 0.8 or less than about 0.6, ethyl cellulose, cellulose nitrate, cellulose acetate butyrate, methyl cellulose, and mixtures thereof.

Representative polyesters include saturated or unsaturated polyesters such as, but not limited to, poly (butylene terephthalate), poly(ethylene 2,6-naphthalene dicarboxylate) (PEN), and poly (ethylene terephthalate).

Representative polyamides include crystalline or amorphous polyamides such as, but not limited to, nylon-6, nylon-6,6, nylon-6,9, nylon-6,10, aromatic nylon MXD6 (manufactured by Mitsubishi Gas Chemical America Inc.), and mixtures thereof.

Representative polyacrylates include, but are not limited to, poly(methylmethacrylate) and polymethacrylate.

In one embodiment, the particle can be a mixture of the aforementioned polymers. For example, the polymer can comprise about 70% to about 99% by weight acrylonitrile and about 30% to about 1% by weight styrene. Similarly, copolymers of vinyl chloride and vinylidene chloride with a vinyl chloride content of about 1 to about 30 mole percent and PET/PHB copolymers with a PHB content of about 60 to about 80 mole percent function effectively.

Examples of the Device

The device or prosthesis used in conjunction with the above-described compositions may be any suitable device used for the release of an active ingredient, examples of which include self-expandable stents, balloon-expandable stents, and stent-grafts, and grafts. The underlying structure of the device can be virtually any design. The device can be made of a metallic material or an alloy such as, but not limited to, cobalt chromium alloy (ELGILOY), stainless steel (316L), "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. A polymeric device should be compatible with the selected compositions. The ethylene vinyl alcohol copolymer, however, adheres very well to metallic materials, more specifically to stainless steel.

Methods for Applying the Compositions to the Device

To form the primer layer, the surface of the device or prosthesis should be clean and free from contaminants that may be introduced during manufacturing. However, the surface of the prosthesis requires no particular surface treatment to retain the applied coating. Metallic surfaces of stents can be, for example, cleaned by argon plasma process as is well known to one of ordinary skill in the art. Application of the composition can be by any conventional method, such as by spraying the composition onto the prosthesis or immersing the prosthesis in the composition. Operations such as wiping, centrifugation, blowing, or other web clearing acts can also be performed to achieve a more uniform coating. Briefly, wiping refers to physical removal of excess coating from the surface of the stent; centrifugation refers to rapid rotation of the stent about an axis of rotation; and blowing refers to application of air at a selected pressure to the deposited coating. The excess coating can also be vacuumed off the surface of the device. The addition of a wetting fluid leads to a consistent application of the composition, which also causes the coating to be uniformly deposited on the surface of the prosthesis.

With the use of the thermoplastic polymers, such as ethylene vinyl alcohol copolymer, polycaprolactone, poly(lactide-co-glycolide), poly(hydroxybutyrate), etc., the deposited primer composition should be exposed to a heat treatment at temperature range greater than about the glass transition temperature ($T_g$) and less than about the melting temperature ($T_m$) of the selected polymer. Unexpected results have been discovered with treatment of the composition under this temperature range, specifically strong adhesion or bonding of the coating to the metallic surface of a stent. The device should be exposed to the heat treatment for any suitable duration of time, which would allow for the formation of the primer coating on the surface of the device and allows for the evaporation of the solvent or combination of solvent and wetting fluid. It is understood that essentially all of the solvent and the wetting fluid will be removed from the composition but traces or residues can remain blended with the polymer.

Table 3 lists the $T_g$ and $T_m$ for some of the polymers used in the embodiments of the present invention. $T_g$ and $T_m$ of polymers are attainable by one or ordinary skill in the art. The cited exemplary temperature and time for exposure is provided by way of illustration and it is not meant to be limiting.

TABLE 3

| Polymer | $T_g$ (° C.) | $T_m$ (° C.) | Exemplary Temperature (° C.) | Exemplary Duration of Time For Heating |
|---|---|---|---|---|
| EVOH | 55 | 165 | 140 | 4 hours |
| polycaprolactone | −60 | 60 | 50 | 2 hours |
| ethylene vinyl acetate (e.g., 33% vinyl-acetate content) | 36 | 63 | 45 | 2 hours |
| Polyvinyl alcohol | 75-85* | 200-220* | 165 | 2 hours |

*Exact temperature depends on the degree of hydrolysis which is also known as the amount of residual acetate.

With the use of one of the aforementioned thermoset polymers, the use of initiators may be required. By way of example, epoxy systems consisting of diglycidyl ether of bisphenol A resins can be cured with amine curatives, thermoset polyurethane prepolymers can be cured with polyols, polyamines, or water (moisture), and acrylated urethane can be cured with UV light. Examples 27 and 28 provide illustrative descriptions. If baked, the temperature can be above the $T_g$ of the selected polymer.

With the use of the inorganic polymers, such as silanes, titanates, and zirconates the composition containing the prepolymer or precursor is applied and the solvent is allowed to evaporate. Example 29 provides a brief description.

Subsequent to the formation of the primer layer, the composition containing the active ingredient can be applied to a designated region of the primer coating. Masking techniques can be implemented for applying compositions containing different active ingredients to selected regions of the primer layer. Accordingly, stents having various cocktail formulations or combinations of a variety of active ingredients can be manufactured. The solvent(s) or the combination of the solvent(s) and the wetting fluid is removed from the composition by allowing the solvent(s) or combination of the solvent(s) and the wetting fluid to evaporate. The evaporation can be induced by heating device at a predetermined temperature for a predetermined period of time. For example, the device can be heated at a temperature of about 60° C. for about 12 hours to about 24 hours. The heating can be conducted in an anhydrous atmosphere and at ambient pressure and should not exceed the temperature which would adversely affect the active ingredient. The heating can, alternatively, be conducted under a vacuum condition. It is understood that essentially all of the solvent and the wetting fluid will be removed from the composition but traces or residues can remain blended with the polymer.

The diffusion barrier layer can be deposited on a designated region of the active ingredient-containing coating subsequent to the evaporation of the solvent(s) or solvent(s)/wetting fluid and the drying of the polymer for the active ingredient-containing coating. The diffusion barrier layer can also be applied by spraying the composition onto the device or immersing the device in the composition. The above-described processes can be similarly repeated for the formation of the diffusion barrier layer.

Coating

Some of the various embodiments of the present invention are illustrated by FIGS. 2A-2E, 3A and 3B. The Figures have not been drawn to scale, and the depth and thickness of the various regions and layers have been over or under emphasized for illustrative purposes.

Figure 2A:
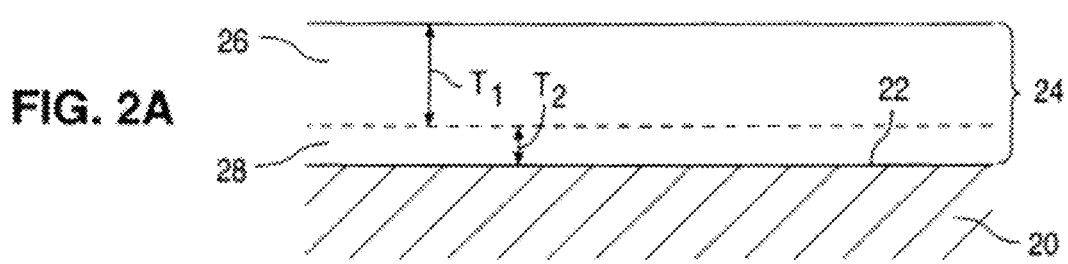
FIGS. 2A-2E illustrate a coating in accordance with some of the embodiment of the present invention.
Figure 2B:
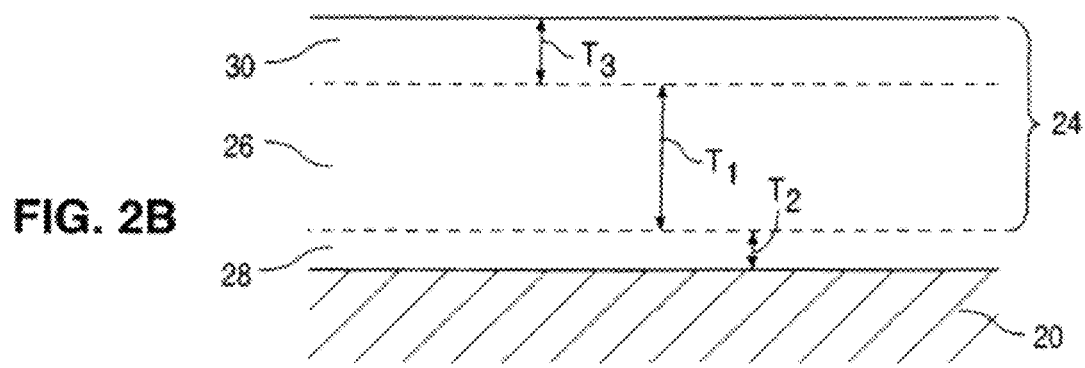

Referring to FIG. 2A, a body of a stent 20 is illustrated having a surface 22, e.g., metallic surface such as stainless steel. A coating 24 is disposed on surface 22. Coating 24 includes a first region 26 defining the reservoir portion of coating 24 containing the active ingredient. A second region 28, free from any active ingredients, defines the primer portion of coating 24. In accordance with another embodiment, as illustrated in FIG. 2B, coating 24 can include a third region 30 defining a barrier portion, free from any particles. Third region 30, as illustrated in FIG. 2C, can also include particles 32.

Figure 2C:
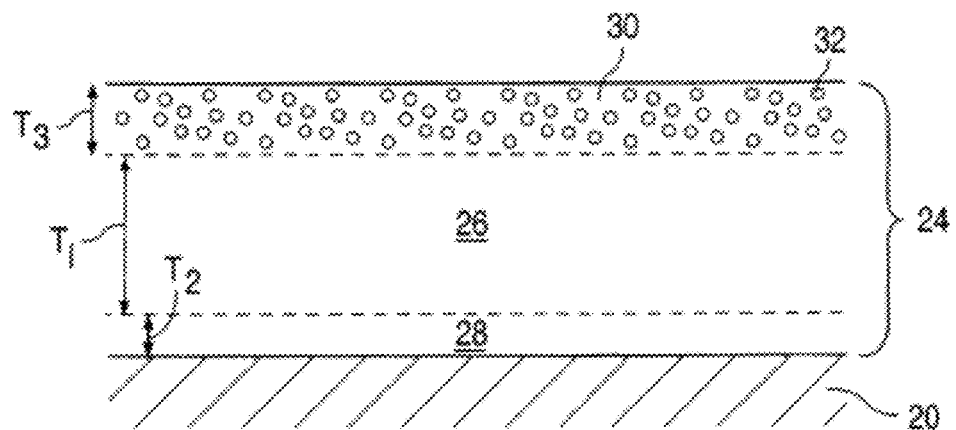

Coating 24 for FIGS. 2A-2C is made from only one of the aforementioned polymeric materials, e.g., EVOH, and accordingly, the existence of any interfacial boundaries between the first 26, second 28, and third 30 regions is essentially reduced or eliminated. Elimination of interfacial boundaries essentially reduces or eliminates any incompatibilities, such as adhesiveness, that may exist when using layers of different polymeric materials.

By way of example, and not limitation, reservoir region 26 for coating 24 can have a thickness $T_1$ of about 0.5 microns to about 10 microns. The particular thickness $T_1$ is based on the type of procedure for which stent 20 is employed and the amount of the active ingredient that is desired to be delivered. Primer region 28 can have any suitable thickness $T_2$, examples of which can be in the range of about 0.1 to about 10 microns, more narrowly about 0.1 to about 2 microns. Diffusion barrier region 30 can have any suitable thickness $T_3$, as the thickness $T_3$ is dependent on parameters such as, but not limited to, the desired rate or duration of release and the procedure for which stent 20 will be used. Diffusion barrier region 30 can have a thickness $T_3$ of about 0.1 to about 10 microns, more narrowly from about 0.25 to about 2 microns. If particles 32 are employed, for a smooth outer surface, the size of particles 32 should not be greater than about 10% of thickness $T_3$ of diffusion barrier region 30. Additionally, the particle volume fraction $X_p$ should not exceed about 0.74. Packing density or particle volume fraction $X_p$ can be defined by the following equation:

$$X_p = V_{particles}/(V_{particles} + V_{polymer})$$

wherein V is volume.

Figure 2D:
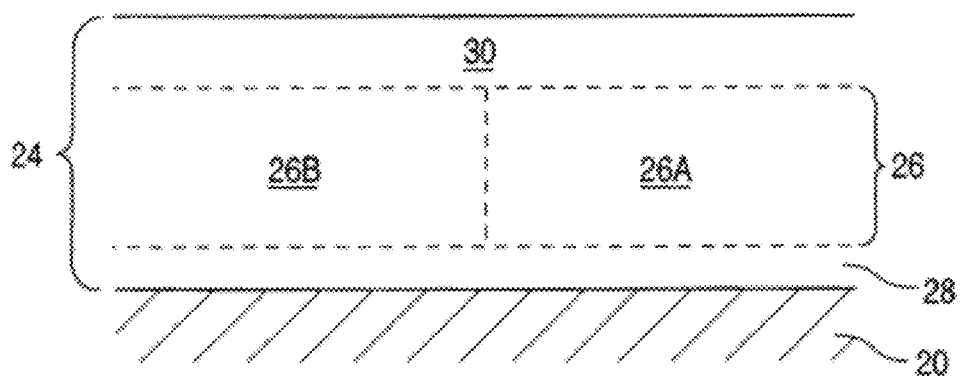

In yet another embodiment, as illustrated in FIG. 2D, reservoir region 26 can include a first and second reservoir sections 26A and 26B, each containing a different active ingredient, e.g., actinomycin D and taxol, respectively. Accordingly, coating 24 can carry a combination of at least two different active ingredients for sustained delivery. First and second sections 26A and 26B can be deposited by, for example, masking the area of primer region 28 over second section 26B and applying a first composition containing a first active ingredient to form first section 26A. First section 26A can then be masked and a second composition containing a second active ingredient can be applied to form second section 26B. This procedure can be followed to from any suitable number of regions containing a different active ingredient.

Figure 2E:
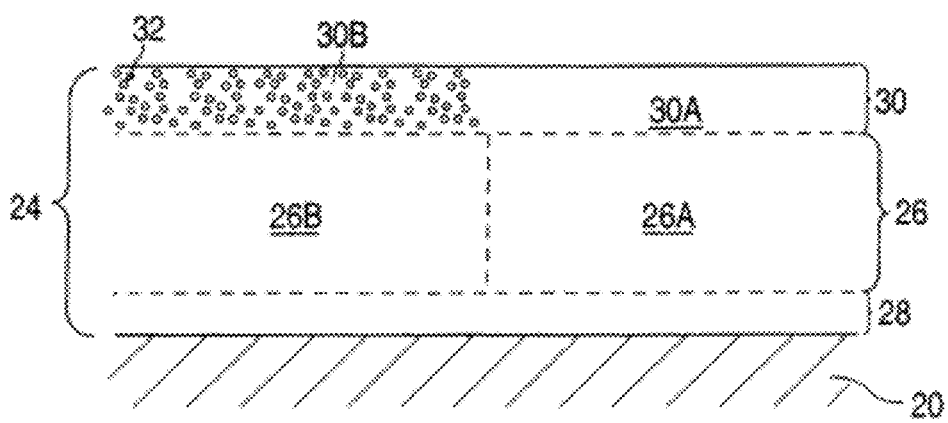

In accordance with yet another embodiment, barrier region 30 can be formed on reservoir sections 26A and 26B, as illustrated in FIG. 2D. Referring to FIG. 2E, barrier region 30 can include a first barrier section 30A disposed over first reservoir section 26A containing a first active ingredient, e.g., actinomycin D. A second barrier section 30B is formed over second reservoir section 26B containing a second active ingredient, e.g., taxol. First barrier section 30A is particle free and second barrier section 30B contains particles 32. As a result, coating 24 harbors two different release parameters for each of the active ingredients contained in reservoir sections 26A and 26B.

Figure 3A:
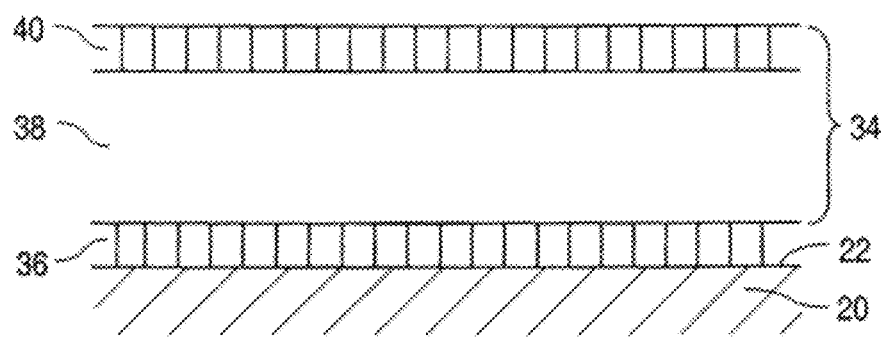
FIGS. 3A and 3B illustrate a coating having different layers.

In accordance with yet another embodiment, different polymeric materials having interfacial compatibilities can be used to form individual, distinct layers for the primer, reservoir, and diffusion barrier components of the coating. Referring to FIG. 3A, a coating 34 is provided having a primer layer 36, made from a first polymeric material, formed on surface 22 of stent 20. A reservoir layer 38 made from a second polymeric material is deposited on a selected area of primer layer 36. A barrier layer 40, made from a third polymeric material can be deposited on reservoir layer 38.

Figure 3B:
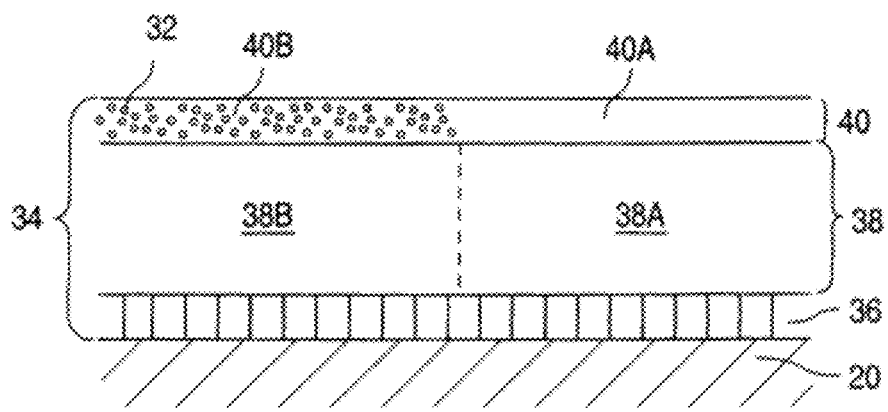

One of ordinary skill in the art can appreciate that a variety of coating combinations can be provided with the practice of the present invention. For example, as illustrated in FIG. 3B, coating 34 contains primer layer 36 made from a first polymeric material. Reservoir layer 38, made from a second polymeric material, is formed on primer layer 36. Reservoir layer 38 contains first and second regions, illustrated as 38A and 38B. First and second regions 38A and 38B each contain a different active ingredient. Barrier layer 40, made from a third polymeric material, can be deposited on reservoir layer 38. Barrier layer 40 includes a first region 40A deposited over first region 38A of reservoir layer 38. Barrier layer 40 additionally includes a second region 40B deposited over second region 38B of reservoir layer 38. Second region 40B can include particles 32 and/or be made out of a fourth polymeric material to create a variety of different release parameters.

Examples of different polymeric materials having interfacial compatibilities include, for example, an EVOH primer with a reservoir layer of ethylene vinylacetate; a poly(n-butyl methacrylate) primer with an EVOH reservoir layer; an EVOH primer and a reservoir layer of polycaprolactone; and an epoxy primer consisting of the diglycidylether of bisphenol A cured with polyamine curatives with an EVOH reservoir layers. Other combinations can be derived by one of ordinary skill in the art.

Method of Use

In accordance with the above-described method, the active ingredient can be applied to a medical device, e.g., a stent, retained on the stent during delivery and expansion of the stent, and released at a desired control rate and for a predetermined duration of time at the site of implantation. A stent having the above-described coating layers is useful for a variety of medical procedures, including, by way of example, treatment of obstructions caused by tumors in bile ducts, esophagus, trachea/bronchi and other biological passageways. A stent having the above-described coating layers is particularly useful for treating occluded regions of blood vessels caused abnormal or inappropriate migration and proliferation of smooth muscle cells, thrombosis, and restenosis.

Stents may be placed in a wide array of blood vessels, both arteries and veins. Representative examples of sites include the iliac, renal, and coronary arteries. The application of the present invention should not, however, be limited to stents such that the embodiments of the coating can be used with a variety of medical substrates.

Briefly, an angiogram is first performed to determine the appropriate positioning for stent therapy. Angiography is typically accomplished by injecting a radiopaque contrast agent through a catheter inserted into an artery or vein as an x-ray is taken. A guidewire is then advanced through the lesion or proposed site of treatment. Over the guidewire is passed a delivery catheter which allows a stent in its collapsed configuration to be inserted into the passageway. The delivery catheter is inserted either percutaneously or by surgery into the femoral artery, brachial artery, femoral vein, or brachial vein, and advanced into the appropriate blood vessel by steering the catheter through the vascular system under fluoroscopic guidance. A stent having the above described coating layers may then be expanded at the desired area of treatment. A post insertion angiogram may also be utilized to confirm appropriate positioning.

EXAMPLES

The embodiments of the invention will be illustrated by the following set forth examples which are being given by way of illustration only and not by way of limitation. All parameters and data are not be construed to unduly limit the scope of the embodiments of the invention.

Example 1

Multi-Link™ stents (available from Guidant Corporation) were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH:DMSO ratio of 1:7. The mixture was placed in a warm water shaker bath at 60° C. for 24 hours. The solution was cooled and vortexed. The cleaned Multi-Link™ stents were dipped in the EVOH solution and then passed over a hot plate, for about 3-5 seconds, with a temperature setting of about 60° C. The coated stents were heated for 6 hours in an air box and then placed in an oven at 60° C., under vacuum condition, and for 24 hours. The coated stents were expanded on a 4.0 mm angioplasty balloon. The coatings remained intact on the stents. The coatings were transparent giving the Multi-Link™ stents a glossy-like shine.

Example 2

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 4 grams of DMSO, making an EVOH:DMSO ratio of 1:4. Dexamethasone was added to the 1:4 EVOH:DMSO solution. Dexamethasone constituted 9% by weight of the total weight of the solution. The solution was vortexed and placed in a tube. The cleaned Multi-Link™ stents were attached to mandrel wires and dipped into the solution. The coated stents were passed over a hot plate, for about 3-5 seconds, with a temperature setting of about 60° C. The coated stents were cured for 6 hours in an air box and then placed in a vacuum oven at 60° C. for 24 hours. The above-recited step was repeated twice. The average weight of the coating was 0.0003 gram, having an estimated dexamethasone content of 75 ug per stent. The coated stents were expanded on a 4.0 mm angioplasty balloon. The coatings remained intact on the stents. Verification of coverage and physical properties of the coatings were visualized using a scanning electron microscope. The coatings were transparent, giving the Multi-Link™ stents a glossy-like shine.

Example 3

Multi-Link Duet™ stents are cleaned by placement in an ultrasonic bath of isopropyl alcohol solution for 10 minutes. The stents are dried and plasma cleaned in a plasma chamber. The EVOH solution is made with 1 gram of EVOH and 4 grams of DMSO, making an EVOH:DMSO ratio of 1:4. Dexamethasone is added to the 1:4 EVOH:DMSO solution. Dexamethasone constitutes 9% by weight of the total weight of the solution. The solution is vortexed and placed in a tube. The cleaned Multi-Link™ stents are attached to mandrel wires and dipped into the solution. The coated stents are passed over a hot plate, for about 3-5 seconds, with a temperature setting of about 60° C. The coated stents are cured for 6 hours in an air box then placed in a vacuum oven at 60° C. for 24 hours. The single layered dexamethasone/EVOH coated stents are dipped into the 1:4 ratio EVOH:DMSO solution, free from dexamethasone. The stents are passed over the hot plate, cured, and placed in the oven as previously described. The top coating will provide a barrier layer for controlling the release of dexamethasone from the drug coated layer. The coated stents can be expanded on a 4.0 mm angioplasty balloon. It is predicted that the coatings will remain intact on the stents. The coatings will be transparent, giving the Multi-Link™ stents a glossy-like shine.

Example 4

Figure 4:
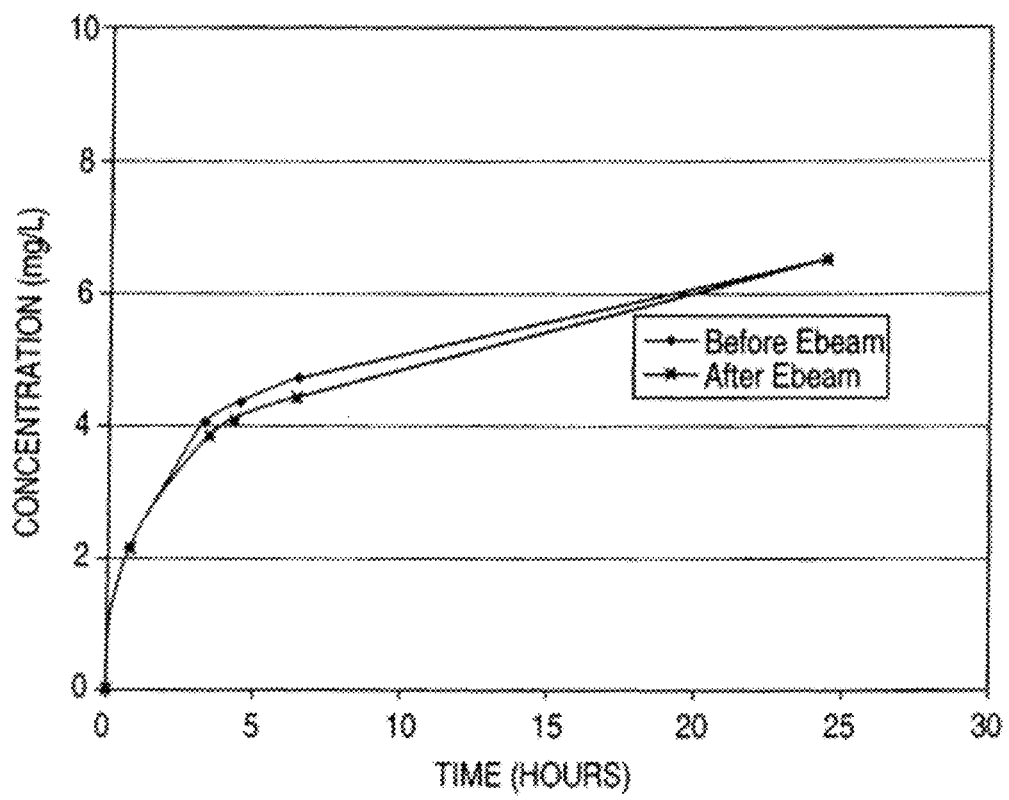
FIG. 4 graphically illustrates elution profiles for stents with a coating of ethylene vinyl alcohol copolymer impregnated with vinblastine made according to Example 4.

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH:DMSO ratio of 1:7. Vinblastine was added to the 1:7 EVOH:DMSO solution. Vinblastine constituted 2.5% by weight of the total weight of the solution. The solution was vortexed and placed in a tube. The cleaned Multi-Link™ stents were attached to mandrel wires and dipped into the solution. The coated stents were passed over a hot plate, for about 3-5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00005 gram, with an estimated vinblastine concentration of 12 microgram per stent. Some of the stents were sterilized by electron beam radiation. The sterilized and unsterilized vinblastine coated stents were tested for a 24 hour elution period by placing one sterilized and one unsterilized stent in 5 ml of phosphated saline solution (pH 7.4) at room temperature with rotational motion. The amount of vinblastine eluted was evaluated by High Performance Liquid Chromatography (HPLC) analysis. The results of this test are given below and plotted in FIG. 4. The data indicates that electron beam radiation procedure does not interfere in the release of vinblastine from EVOH.

| Release Profile For Vinblastine -- Unsterilized | | | |
|---|---|---|---|
| Time (Hours) | microgram Released | Total microgram Released | microgram Release per Hour |
| 0 | 0 | 0 | 0 |
| 0.5 | 2.12 | 2.12 | 4.24 |
| 3 | 1.91 | 4.03 | 0.76 |
| 4 | 0.27 | 4.30 | 0.27 |
| 6 | 0.38 | 4.68 | 0.19 |
| 24 | 1.7 | 6.38 | 0.09 |

| Release Profile For Vinblastine -- Sterilized | | | |
|---|---|---|---|
| Time (Hours) | ug Release | Total uG Released | uG Release per Hour |
| 0 | 0 | 0 | 0 |
| 0.5 | 2.14 | 2.14 | 4.28 |
| 3 | 1.7 | 3.84 | 0.68 |
| 4 | 0.28 | 4.12 | 0.28 |
| 6 | 0.26 | 4.38 | 0.13 |
| 24 | 2.05 | 6.43 | 0.11 |

Example 5

Multi-Link™ stents were cleaned by placement in an ultrasonic bath of isopropyl alcohol solution for 10 minutes. The stents were dried and plasma cleaned in a plasma chamber. An EVOH solution was made with 1 gram of EVOH and 7 grams of DMSO, making an EVOH:DMSO ratio of 1:7. Cephalotaxin was added to the 1:7 EVOH:DMSO solution. Cephalotaxin constituted 5% by weight of the total weight of the solution. The solution was vortexed and placed in a tube. The cleaned Multi-Link™ stents were attached to mandrel wires and dipped into the solution. The coated stents were passed over a hot plate, for about 3-5 seconds, with a temperature setting of about 60° C. The coated stents were cured for 6 hours in an air box then placed in a vacuum oven at 60° C. for 24 hours. The above process was repeated twice, having a total of three layers. The average weight of the coating was 0.00013 gram, with an estimated cephalotaxin concentration of 33 ug. The stents were sterilized by electron beam radiation. Cephalotaxin/EVOH coated stents and EVOH-coated control stents were implanted in the coronary arteries of 4 pigs, generally in accordance to the procedure set forth in "Restenosis After Balloon Angioplasty—A Practical Proliferative Model in Porcine Coronary Arteries" by Robert S. Schwartz, et al., Circulation 82(6):2190-2200, December 1990, and "Restenosis and the Proportional Neointimal Response to Coronary Artery Injury: Results in a Porcine Model" by Robert S. Schwartz et al, J Am Coll Cardiol; 19:267-74 Feb. 1992. Results of the porcine artery study indicated that there was no significant difference between the uncoated, EVOH coated and cephalotaxin coated stents in the amount of neointimal proliferation resulting from arterial injury.

Example 6

Multi-Link Duet™ stents (available from Guidant Corporation) were cleaned by placement in an ultrasonic bath of isopropyl alcohol solution for 20 minutes, then air dried. An EVOH stock solution was made with 1 gram of EVOH and 7 grams of DMSO, making an EVOH:DMSO ratio of 1:7. The mixture was placed in a warm water shaker bath at 60° C. for 12 hours. The solution was mixed, then cooled to room temperature. A co-solvent was added to the EVOH solution to promote wetting of the struts of the Multi-Link Duet™ stents. One gram of tetrahydrofuran (THF) was mixed with 1.2 grams of the EVOH:DMSO solution. The cleaned Multi-Link Duet™ stents were attached to mandrel wires and dipped into the solution. The coated stents were passed over a hot plate, for about 3 to 5 seconds, with a temperature setting of about 60° C. The coated stents were then heated in a laboratory oven at 90° C. for 4 hours. The thin EVOH coating adhered to stainless steel without peeling or cracking. EVOH forms a superior primer base coat for other polymers that do not adhere well to stainless steel.

Example 7

Multi-Link Duet™ stents were cleaned in an ultrasonic bath of isopropyl alcohol for 20 minutes, then air dried. An EVOH solution was made with 1 gram of EVOH and 5 grams of DMSO, making an EVOH:DMSO ratio of 1:5. The mixture was placed in a warm water shaker bath at 60° C. for 12 hours. The solution was mixed, then cooled to room temperature. The dissolved EVOH:DMSO solution was mixed with 24.6 grams of THF and 19.56 grams of DMSO. The solution was mixed then placed in the reservoir of an air pressured atomizing sprayer. Multi-Link Duet™ stents were sprayed while the stents rotated between 30 to 120 rpm. The spray time was dependent upon the flow rate of the sprayer. A flow rate between 1 to 20 mg/second required a stent to be sprayed between 1 to 30 seconds. The polymer coated Multi-Link Duet™ stents were heated in a forced air convection oven for 12 hours. The coatings were transparent, giving the Multi-Link Duet™ stents a glossy-like shine.

Example 8

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. Various co-solvents were examined to determine which co-solvent would promote a thicker coating. These co-solvents were THF, DMF, 1-butanol, and n-butyl acetate. The formulation for the co-solvents was as follows. Three grams of dissolved EVOH:DMSO solution was mixed with 0.9 gram of THF; three grams of dissolved EVOH:DMSO solution was mixed with 0.39 gram of DMF; three grams of dissolved EVOH:DMSO solution was mixed with 0.5 gram of 1-butanol; and three grams of dissolved EVOH:DMSO solution was mixed with 0.68 gram of n-butyl acetate. The cleaned Multi-Link Duet™ stents, attached to mandrel wires, were dipped into the solutions. The coated stents were passed over a hot plate, for about 3 to 5 seconds, with a temperature setting of about 60° C. The coated stents were heated in a forced air convection oven for 24 hours. A second layer of coating was applied to coated Multi-Link Duet™ stents and the stents were heated in the same manner as above. No difference was seen between the stents coated with the various co-solvents (e.g., greater weight of coating or physical appearance). All coated stents were transparent, giving the Multi-Link Duet™ stents a glossy-like shine. No webbing or bridging of the coating was seen between the struts of the coated Multi-Link Duet™ stents. The weight of the coatings was between 0.2 to 0.27 mg/stent.

Example 9

Multi-Link Duet™ stents are cleaned in an ultrasonic bath of isopropyl alcohol for 20 minutes, then air dried. An EVOH stock solution is made having an EVOH:DMSO ratio of 1:4. The mixture is placed in a warm water shaker bath at 60° C. for 12 hours. The solution is mixed, then cooled to room temperature. A 9% by weight Dexamethasone solution is formulated as follows: 2.96 grams of the EVOH:DMSO solution is mixed with 0.29 gram of Dexamethasone, then 0.9 gram of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

Example 10

Multi-Link Duet™ stents are cleaned in an ultrasonic bath of isopropyl alcohol for 20 minutes, then air dried. An EVOH stock solution is made having an EVOH:DMSO ratio of 1:4. The mixture is placed in a warm water shaker bath at 60° C. for 12 hours. The solution is mixed, then cooled to room temperature. A 9% by weight Dexamethasone solution is formulated as follows: 2.96 grams of the EVOH:DMSO solution is mixed with 0.29 gram of Dexamethasone, then 0.9 gram of THF is added. The cleaned Multi-Link Duet™ stents are attached to mandrel wires and dipped into the solution. The coated stents are passed over a hot plate, for about 3 to 5 seconds, with a temperature setting of about 60° C. The coated stents are cured in a forced air convection oven for 2 hours. A second layer of coating is applied and cured in the above manner. It is predicted that the coatings will be transparent, giving the Multi-Link Duet™ stents a glossy-like shine.

Example 11

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 4.75% by weight actinomycin D solution was formulated as follows: 600 milligrams of the EVOH:DMSO solution was mixed with 40 milligrams of actinomycin D, then 200 milligrams of THF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 12

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 3.60% by weight actinomycin D solution was formulated as follows: 600 milligrams of the EVOH:DMSO solution was mixed with 40 milligrams of actinomycin D, then 480 milligrams of DMF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 13

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 6.45% by weight actinomycin D solution was formulated as follows: 680 milligrams of the EVOH:DMSO solution was mixed with 80 milligrams of actinomycin D, then 480 milligrams of DMF was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven for 2 hours. A second layer of coating was applied and cured in the above manner.

Example 14

Multi-Link Duet™ stents are cleaned in an ultrasonic bath of isopropyl alcohol for 20 minutes, then air dried. An EVOH stock solution is made having an EVOH:DMSO ratio of 1:40. The mixture is placed in a warm water shaker bath at 60° C. for 12 hours. The solution is mixed, then cooled to room temperature. A 0.60% by weight actinomycin D solution can be formulated as follows: 4920 milligrams of the EVOH:DMSO solution is mixed with 40 milligrams of Actinomycin D, then 2000 milligrams of THF is added. The cleaned Multi-Link Duet™ stents can be sprayed upon by the above formulation. The coated stents are cured in a forced air convection oven for 2 hours. A second layer of coating is applied and cured in the above manner.

Example 15

Inhibition of SMC Proliferation with Actinomycin D

Figure 5:
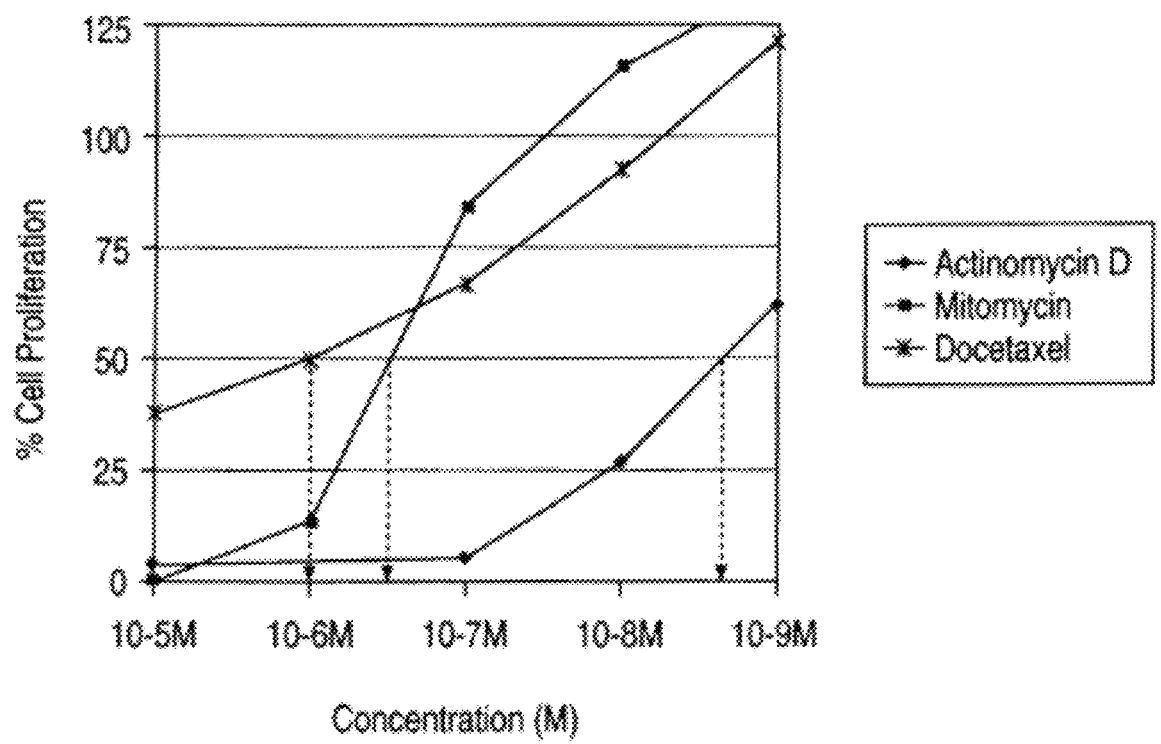
FIG. 5 graphically illustrates in vitro experimental data, in accordance with Example 15, showing affects of actinomycin D, mitomycin, and docetaxel on smooth muscle cell proliferation.

Medial smooth muscle cells (SMC) were isolated from rat aorta and cultured according to explant methods known to one of ordinary skill in the art. Cells were harvested via trypsinization and subcultivated. Cells were identified as vascular SMC through their characteristic hill-and-valley growth pattern as well as indirect immunofluorescence with monoclonal anti SMC α-actin. Studies were performed with cells at passage 3-4. SMC monolayers were established on 24 well culture dishes, scrape wounded and treated with actinomycin D, mytomycin and docetaxel. The cells were exposed to the drug solution of different concentrations for 2 hours and then washed with buffered saline solution. The proliferation of the cells was quantified by standard technique of thymidine incorporation. The results from the study are tabulated in FIG. 5.

The $IC_{50}$ (concentration at which 50% of the cells stop proliferating) of actimomycin D was $10^{-9}$M as compared to $5\times10^{-5}$M for mitomycin and $10^{-6}$M for docetaxel. Actinomycin D was the most potent agent to prevent SMC proliferation as compared to other pharmaceutical agents.

Example 16

Reduction in Restenosis in the Porcine Coronary Artery Model

Porcine coronary models were used to assess the degree of the inhibition of neointimal formation in the coronary arteries of a porcine stent injury model by Actinomycin D, delivered with a microporous balloon catheter ($1\times10^6$ pores/mm$^2$ with sizes ranging from 0.2-0.8 micron).

The preclinical animal testing was performed in accordance with the NIH Guide for Care and Use of Laboratory Animals. Domestic swine were utilized to evaluate effect of the drug on the inhibition of the neointimal formation. Each testing procedure, excluding the angiographic analysis at the follow-up endpoints, was conducted using sterile techniques. During the study procedure, the activated clotting time (ACT) was monitored regularly to ensure appropriate anticoagulation. Base line blood samples were collected for each animal before initiation of the procedure. Quantitative coronary angiographic analysis (QCA) and intravascular ultrasound (IVUS) analysis was used for vessel size assessment.

The vessels at the sites of the delivery were denuded by inflation of the PTCA balloons to 1:1 balloon to artery ratio and moving the balloons back and forth 5 times. The drug was delivered to the denuded sites at 3.5 atm (3.61 Kg/sq cm) for 2 minutes using the microporous balloon catheters before stent deployment. The average volume of delivery was about 3.3+/−1.2 ml. Following drug delivery, stents were deployed at the delivery site such that final stent to artery ratio was 1.1:1.

QCA and IVUS analyses were used for stent deployment guidance. Pre-stenting IVUS measurements of the lumen size at the targeted vessel sites were performed for determination of the balloon (size) inflation pressure. Quantitative analysis of the stented coronary arteries to compare pre-stenting, post-stenting, follow-up minimal luminal diameters, stent recoil, and balloon/stent to artery ratio were performed. Following stent implantation and final angiogram, all devices were withdrawn and the wounds closed; the animals were allowed to recover from anesthesia as managed by the attending veterinarian or animal care professionals at the research center.

Upon return to the research laboratory at the 28-day endpoint, angiographic assessments were performed. Coronary artery blood flow was assessed and the stented vessels were evaluated to determine minimal lumen diameter. The animals were euthanized following this procedure at the endpoint. Following euthanasia, the hearts were pressure perfusion fixed with formalin and prepared for histological analysis, encompassing light microscopy, and morphometry. Morphometric analysis of the stented arteries included assessment of the position of the stent struts and determination of vessel/lumen areas, percent (%) stenosis, injury scores, intimal and medial areas and intima/media ratios. Percent stenosis is quantitated by the following equation:

$$100(\text{IEL area}-\text{lumen area})/\text{IEL area}$$

where IEL is the internal elastic lamia.

The control group of animals received delivery of water instead of the drug. The test group of animals received actinomycin D in two different concentration of $10^{-5}$M and $10^{-4}$M. The results of the study are tabulated in Table 4. The percent stenosis in the treated groups (32.3+/−11.7) was significantly decreased as compared to the control groups (48.8+/−9.8). FIGS. 6A and 6B illustrate sample pictures of the histology slides of the coronary vessels from the control and the Dose 1 group, respectively.

TABLE 4

|  | CONTROL 0M | DOSE 1 1E-05M | DOSE 2 1E-04M | t test (significant if p < 0.05) | |
| --- | --- | --- | --- | --- | --- |
|  | (n = 9) | (n = 10) | (n = 7) | p~ | p* |
| ANGIOGRAPHIC DATA (QCA) | | | | | |
| Percent Diameter Stenosis | 48.8 +/− 9.8 | 36.8 +/− 9.7 | 32.3 +/− 11.7 | 0.02 | 0.01 |
|  | CONTROL 0M | DOSE 1 1E-05M | DOSE 2 1E-04M | t test (significant if p < 0.05) | |
|  | (n = 27) | (n = 30) | (n = 21) | p~ | p* |
| HISTOMORPHOMETRIC DATA | | | | | |
| Percent Stenosis (IEL area-lumen area)/IEL area | 63.4 +/− 12.7 | 51.8 +/− 13.8 | 54.1 +/− 11.7 | 0.002 | 0.01 |
| Residual Lumen (Lumen area)/IEL area | 0.36 +/− 0.16 | 0.49 +/− 0.14 | 0.46 +/− 0.08 | 0.002 | 0.01 |

~comparison between control and Dose 1
*comparison between control and Dose 2

The results of the in vitro and in vivo standard test procedures demonstrate that actinomycin D is useful for the treatment of hyper-proliferative vascular disease. Specifically, actinomycin D is useful for the inhibition of smooth muscle cell hyperplasia, restenosis and vascular occlusion in a mammal, particularly occlusions following a mechanically mediated vascular trauma or injury.

Example 17

Multi-Link Duet™ stents (13 mm in length) were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 5.06% by weight actinomycin D solution was formulated as follows: 40 milligrams of actinomycin D was dissolved in 150 milligrams of THF, then 600 milligrams of the EVOH:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 260 micrograms and an average actinomycin D loading of about 64 micrograms was achieved.

Example 18

Multi-Link Duet™ stents (13 mm in length) were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 3.75% by weight actinomycin D solution was formulated as follows: 60 milligrams of actinomycin D was dissolved in 310 milligrams of DMF, then 1.22 grams of EVOH:DMSO solution was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 270 micrograms with an average actinomycin D content of about 51 micrograms was achieved.

Example 19

Multi-Link Duet™ stents were cleaned in an ultrasonic bath of isopropyl alcohol for 20 minutes, then air dried. An EVOH stock solution was made having an EVOH:DMSO ratio of 1:4. The mixture was placed in a warm water shaker bath at 60° C. for 12 hours. The solution was mixed, then cooled to room temperature. A 6.1% by weight actinomycin D solution was formulated as follows: 100 milligrams of actinomycin D was dissolved in 310 milligrams of DMF, then 1.22 grams of EVOH:DMSO was added. The cleaned Multi-Link Duet™ stents were attached to mandrel wires and dipped into the solution. The coated stents were passed over a hot plate, for about 3 to 5 seconds, with a temperature setting of about 60° C. The coated stents were cured in a forced air convection oven at 60° C. for 1 hour. A second layer of coating was applied in the above manner and cured in a forced air convection oven at 60° C. for 4 hours. An average coating weight of about 250 micrograms and an average actinomycin D loading of about 75 micrograms was achieved.

Example 20

Multi-Link Duet™ stents are cleaned in an ultrasonic bath of isopropyl alcohol for 20 minutes, then air dried. An EVOH stock solution is made having an EVOH:DMSO ratio of 1:40. The mixture is placed in a warm water shaker bath at 60° C.

for 12 hours. The solution is mixed, then cooled to room temperature. A 0.60% by weight actinomycin D solution can be formulated as follows: 4920 milligrams of the EVOH:DMSO solution is mixed with 40 milligrams of Actinomycin D, then 2000 milligrams of THF is added. The cleaned Multi-Link Duet™ stents can be sprayed upon by the above formulation. The coated stents are cured in a forced air convection oven 60° C. for 15 minutes. Additional layers of the coating are applied and cured in the above manner. The final curing step for the coated stents is conducted for about 4 hours.

Example 21

A stainless steel stent can be spray coated with a formulation of EVOH and a drug, as previously described in any of the above examples. A diffusion barrier composition can be formulated with 2 grams of EVOH blended with 20 grams of dimethylsulfoxide. 2.2 grams of fumed silica can be added and dispersed with a high shear process. With constant agitation, 50 grams of tetrahydrofuran and 30 grams of dimethylformamide are admixed with the blend. The stent, having the EVOH coating, can be immersed in the diffusion barrier composition to form a layer.

Example 22

A stainless steel stent can be spray coated with a formulation of EVOH and a drug, as previously described in any of the above examples. A diffusion barrier formulation can be made by dissolving 8 grams of EVOH into 32 grams of dimethylsulfoxide. To this is added 14 grams of rutile titanium dioxide and 7 grams more of dimethylsulfoxide. The particles can be dispersed using a ball mill. The final solution is diluted with 39 grams of tetrahydrofuran, added slowly with constant agitation. It is predicted that the diffusion barrier will reduce the rate at which the drug is released from the stent.

Example 23

A stainless steel stent can be coated with a formulation of EVOH and a drug, as previously described in any of the above examples. A diffusion barrier formulation can be made by dissolving 8 grams of EVOH in 32 grams of dimethylsulfoxide. 10.5 grams of solution precipitated hydroxyapatite can be added to the blend. The particles can be dispersed using a rotor stator mixer. With constant agitation, 30 grams of tetrahydrofuran can be added. The stent can be coated by immersion followed by centrifugation.

Examples 24

A stent can be coated with a formulation of EVOH and a drug, as previously described in any of the above examples. 8 grams of EVOH can be added 50 grams of dimethylsulfoxide and the polymer can be dissolved by agitation and heat. Four grams of lamp black can be added and dispersed in a ball mill. 60 grams of dimethyl sulfoxide and 110 grams of tetrahydrofuran are slowly added while stirring. The stent can be spray coated.

Example 25

A stent can be coated with a formulation of EVOH and a drug, as previously described in any of the above examples. Colloidal gold can be prepared by reduction of tetrachloroauric acid with sodium citrate in aqueous solution. The solution can be exchanged by rinsing with tetrahydrofuran. Eight grams of EVOH can be dissolved in 32 grams of dimethylsulfoxide. To this is added a solution of 77 grams of colloidal gold in 32 grams of tetrahydrofuran. The stent can be coated by a dip coating process.

Example 26

In vivo data is provided illustrated positive remodeling caused by the application of actinomycin D. Stents coated with EVOH impregnated with actinomycin D and a control group of stents coated with EVOH free from actinomycin D were implanted in porcine coronary arteries. The animals were sacrificed at the end of 28 days. The EEL area of the actinomycin D-loaded vessels was statistically significantly greater than the EEL area of the control vessels. The index of remodeling was 1.076 (8.54/7.94).

| Condition | Mean Area | Std Dev |
|---|---|---|
| IEL | | |
| Drug coated(Act-D in EVOH) | 7.47 | 0.89 |
| Control (EVOH) | 6.6 | 0.61 |
| p value | 0.0002 | Statistical significant difference |
| EEL (external elastic lamia) | | |
| Drug coated(Act-D in EVOH) | 8.54 | 0.87 |
| Control (EVOH) | 7.94 | 0.73 |
| p value | 0.014 | Statistical significant difference |

| EEL Area (mm$^2$) | | | | | |
|---|---|---|---|---|---|
| ID # | Control | ID # | Actinomycin D | ID # | EVOH |
| 48 LCX d | 6.3966 | 63 LCX d | 7.4498 | 63 LAD d | 8.3037 |
| 48 LCX m | 7.4601 | 63 LCX m | 8.2509 | 63 LAD m | 8.8545 |
| 48 LCX p | 7.3063 | 63 LCX p | 7.7342 | 63 LAD p | 9.4698 |
| 49 LAD d | 8.5573 | 63 RCA d | 7.9207 | 64 LCX d | 7.8063 |
| 49 LAD m | 8.5187 | 63 RCA m | 6.9926 | 64 LCX m | 7.1117 |
| 49 LAD p | 6.6346 | 63 RCA p | 8.3883 | 64 LCX p | 7.2411 |
| 58 LAD d | 8.6078 | 65 LAD d | 7.8546 | 64 RCA d | 8.3383 |
| 58 LAD m | 8.1674 | 65 LAD m | 9.2545 | 64 RCA m | 8.0793 |
| 58 LAD p | 8.3775 | 65 LAD p | 9.2515 | 64 RCA p | 8.3652 |
| 59 LCA d | 8.3054 | 68 LAD d | 8.7854 | 65 LCX d | 6.4638 |
| 59 LCX m | 7.3713 | 68 LAD m | 9.5164 | 65 LCX m | 7.1493 |
| 59 LCX p | 7.8662 | 68 LAD p | 9.1504 | 65 RCA d | 8.5955 |
| 59 RCA d | 7.3714 | 69 LCX d | 9.6679 | 65 RCA m | 8.0855 |
| 59 RCA m | 6.6783 | 69 LCX m | 9.1237 | 65 RCA p | 8.4785 |
| 59 RCA p | 7.4707 | 69 LCX p | 9.9849 | 68 LCX d | 8.4723 |
| 62 LCX d | 7.8784 | 69 RCA d | 9.4765 | 68 LCX m | 7.8382 |
| 62 LCX m | 7.5318 | 69 RCA m | 7.4424 | 68 LCX p | 8.0570 |
| 62 LCX p | 6.2647 | 69 RCA p | 9.1462 | 68 RCA d | 8.4840 |
| 62 RCA d | 8.3240 | 70 LCX d | 8.9504 | 68 RCA p | 8.8767 |
| 62 RCA m | 7.9535 | 70 LCX m | 8.9117 | 69 LAD d | 6.6648 |
| 62 RCA p | 8.5454 | 70 LCX p | 8.7533 | 69 LAD m | 6.8614 |
| 67 LAD d | 8.9532 | 70 RCA d | 7.3249 | 69 LAD p | 7.7632 |
| 67 LAD m | 9.2410 | 70 RCA m | 7.1061 | 70 LAD d | 7.5175 |
| 67 LAD p | 8.3841 | 70 RCA p | 8.5830 | 70 LAD m | 7.8630 |
| | | | | 70 LAD p | 8.2222 |
| AVG | 7.8402 | | 8.5425 | | 7.9475 |
| SD | 0.8046 | | 0.8755 | | 0.7349 |

| ActD vs EVOH | |
| --- | --- |
| p = | 0.014709 |
| AVG % EEL growth | 7.486304 |

| IEL Area (mm2) | | | | | |
| --- | --- | --- | --- | --- | --- |
| ID # | Control | ID # | Actinomycin D | ID # | EVOH |
| 48 LCX d | 5.2178 | 63 LCX d | 6.3785 | 63 LAD d | 6.9687 |
| 48 LCX m | 6.2108 | 63 LCX m | 7.5206 | 63 LAD m | 7.3908 |
| 48 LCX p | 6.1125 | 63 LCX p | 6.9992 | 63 LAD p | 7.3563 |
| 49 LAD d | 7.2848 | 63 RCA d | 6.9632 | 64 LCX d | 6.4420 |
| 49 LAD m | 7.4117 | 63 RCA m | 6.0418 | 64 LCX m | 6.0064 |
| 49 LAD p | 5.9918 | 63 RCA p | 7.4794 | 64 LCX p | 5.9970 |
| 58 LAD d | 7.2049 | 65 LAD d | 6.2324 | 64 RCA d | 6.8001 |
| 58 LAD m | 6.9334 | 65 LAD m | 8.3785 | 64 RCA m | 6.8561 |
| 58 LAD p | 6.9454 | 65 LAD p | 8.5819 | 64 RCA p | 7.0172 |
| 59 LCA d | 7.2640 | 68 LAD d | 8.0964 | 65 LCX d | 5.2485 |
| 59 LCX m | 6.2014 | 68 LAD m | 8.6879 | 65 LCX m | 6.1135 |
| 59 LCX p | 6.7283 | 68 LAD p | 8.0914 | 65 RCA d | 7.1525 |
| 59 RCA d | 6.0519 | 69 LCX d | 8.7181 | 65 RCA m | 6.4815 |
| 59 RCA m | 5.9992 | 69 LCX m | 8.0273 | 65 RCA p | 7.1775 |
| 59 RCA p | 5.9032 | 69 LCX p | 8.5222 | 68 LCX d | 6.9571 |
| 62 LCX d | 6.5329 | 69 RCA d | 8.3796 | 68 LCX m | 6.5724 |
| 62 LCX m | 6.2804 | 69 RCA m | 6.4219 | 68 LCX p | 6.7740 |
| 62 LCX p | 4.9303 | 69 RCA p | 7.7757 | 68 RCA d | 7.2425 |
| 62 RCA d | 7.0977 | 70 LCX d | 7.5392 | 68 RCA p | 7.5554 |
| 62 RCA m | 6.7466 | 70 LCX m | 7.6573 | 69 LAD d | 5.5505 |
| 62 RCA p | 7.1747 | 70 LCX p | 6.9749 | 69 LAD m | 5.5571 |
| 67 LAD d | 8.0264 | 70 RCA d | 6.2815 | 69 LAD p | 6.2697 |
| 67 LAD m | 8.1144 | 70 RCA m | 5.9760 | 70 LAD d | 6.3212 |
| 67 LAD p | 7.2091 | 70 RCA p | 7.6195 | 70 LAD m | 6.6518 |
| | | | | 70 LAD p | 6.9032 |
| AVG | 6.6489 | | 7.4727 | | 6.6025 |
| SD | 0.7883 | | 0.8972 | | 0.6130 |

| ActD vs EVOH | |
| --- | --- |
| p = | 0.000283 |
| AVG % IEL growth | 13.17981 |

Figure 7B:
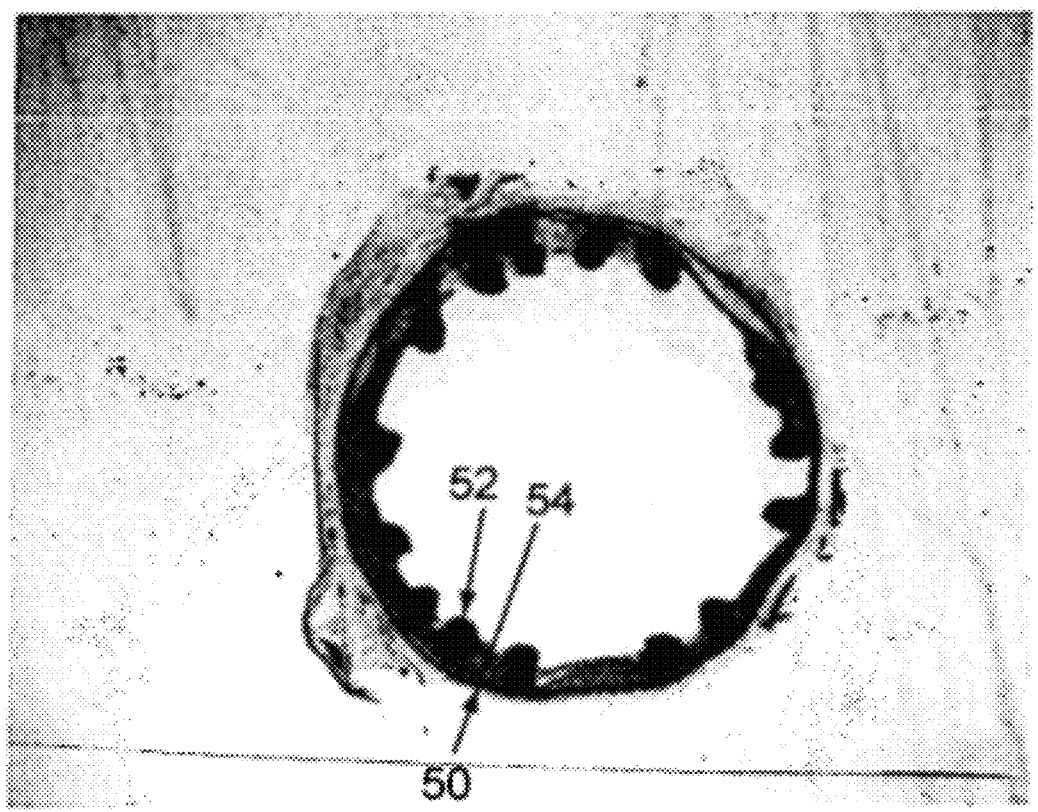
FIG. 7B is a picture of a histology slide of a coronary vessel from the actinomycin D group in accordance with Example 26.

FIGS. 7A and 7B illustrate sample pictures of the histology slides of the coronary vessels from the control group 64 RCA (Right Coronary Group) and the actinomycin D loaded stent group 68 LAD (Left Anterior Descending), respectively. The stent used was an Advanced Cardiovascular Systems Multi-Link Duet™ (stainless steel). As is illustrated by FIG. 7B, the positive remodeling of EEL 50, caused by the application of actinomycin D, creates a gap between stent struts 52 and EEL 50. Thrombus deposites, illustrated by reference number 54, are formed in the gap over time. The use of a self-expandable stent eliminates the formation of the gap as the stent self-expands in response to the positive remodeling of IEL. Thrombus deposits can be, accordingly, eliminated.

Actinomycin D induces the positive remodeling of the vessel walls, more particularly positive remodeling of the external elastic lamina (EEL) of a blood vessel wall. Positive remodeling is generally defined as the ability of the vessel walls to structurally adapt, by increasing in lumen size, to chronic stimuli. A positively remodeled lumen wall has a greater diameter or size as compared to a lumen wall which has not been subjected to the remodeling effect. Accordingly, the flow of blood through the remodeled site is increased—flow which would have otherwise been reduced because of, for example, the presence of plaque build-up or migration and proliferation of cells. The index of remodeling is defined by the ratio of the area circumscribed by the EEL of the lesion site to the area circumscribed by the EEL of a reference site. As a result of the positive remodeling of the EEL, the internal elastic lamina (IEL), in response, can also increases in area or diameter. Actinomycin D, or analogs or derivative thereof, not only can inhibit abnormal or inappropriate migration and/or proliferation of smooth muscle cells, which can lead to restenosis, but can also induce positive remodeling of the blood vessel walls. Thus the widening of the diseased region becomes more pronounced.

Example 27

2 grams of an acrylate terminated urethane (Henkel 12892) can be added to 18 grams of ethyl acetate with 0.08 grams of benzophenone and 0.08 grams of 1-hydroxycyclohexyl phenyl ketone. After application, the stent can be cured for 5 minutes under medium pressure mercury lamp.

Example 28

For a thermoset system, 1.67 grams of Epon 828 (Shell) resin can be added to 98 grams of propylene glycol monomethyl ether and 0.33 grams of Jeffamine T-430 (Huntsman). After application, the stent can be baked for 2 hours at 80° C. and 2 hours at 160° C.

Example 29

A 0.25% (w/w) solution of tetra-n-butyl titanate can be made in anhydrous ethyl acetate. The solution can be applied by spraying to a surface of a stainless steel stent. The stent can be heated at 100° C. for two hours.

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

Example 30

Objective
Coated stents tested through simulated delivery to a target lesion for testing the mechanical integrity of the coating.

| Group | Quantity | Coating |
| --- | --- | --- |
| A | 2 | Control: 2% EVAL in 1:1 THF:DMSO, 3:1 EVAL:Act-d; no primer |
| B | 2 | 2% EVAL in 5:3:2 THF:DMF:DMSO, 3:1 EVAL:Act-d; no primer |
| C | 2 | EVAL primer layer baked at 120 C./60 C. for 2/10 hrs + 2% EVAL in 1:1 THF:DMSO, 3:1 EVAL:Act-d; primer |
| D | 2 | EVAL primer layer baked at 140 C./60 C. for 2/2 hrs + 2% EVAL in 1:1 THF:DMSO, 3:1 EVAL:Act-d; primer |

Background
In this experiment four different treatment groups were tested through a simulated delivery and use. Number of peel defects at rings 3, 5, and 7, with a peel defect defined as a location on the stent where coating has been removed to expose bare stent or an underlying layer of coating, were observed.

Materials and Equipment
1. 8, 13 mm Solo stents (Available from Guidant Corporation);
2. 8, 3.0×30 mm Duet catheters;
3. 100% IPA;
4. Tominator Stent Crimper S/N 400;
5. 7F JL4 guiding catheter;
6. 0.014" Balance Middle Weight guide wire;
7. Rotating Hemostatic Valve;
8. SVS tortuosity tree (2.5 mm lumen tapering to 1.5 mm lumen);

Preparation

Crimped the stents onto the catheters using the Tominator crimper and the following conditions: 3 crimps, 65 psi, rotation between crimps.

Test Procedure
1. Performed simulation using heart model having a tortuosity and contained in a tub filled with water:
   a. Inserted the stents through the following set-up: RHF, 7F JL4 guiding catheter, SVS tortuosity tree (2.5 mm lumen at entrance, 1.5 mm lumen at exit).
   b. Once the stent passed through the distal opening of tortuosity, the balloon was cut from the catheter just distal to proximal marker.
2. Examined the stents under 100× magnification using Leica MZFLIII microscope in the clean environment room (CER).
3. Recorded number of peel defects at stent rings 3, 5, and 7. Only the outer diameter ("OD") was examined for peel defects.
4. All test samples were handled with personal protective equipment (PPE) appropriate for drug containing stents.

Data Summary and Results

| Group | # Peel Defects/Ring | Comments |
| --- | --- | --- |
| A (THF) | 2.0 | — |
| B (DMF) | 5.3 | Began with poor coating finish. |
| C (140° C.) | 0.7 | — |
| D (120° C.) | 0 | — |

Discussion

The test was performed to observe the coating integrity after a simulated delivery to a tortuosity without a lesion. The primer layer improved coating adhesion to the stents that resulted in fewer defects after a simulated use. Group B had a number defects. Although the coating surface for Group B was poor to begin with, and the defects were not too severe.

Example 31

Objective

The adhesion of 0.67% Actinomycin-D (in 5% EVAL 1:1 THF:DMSO solution) coating on stents with two different surface treatments was compared to control samples. The specific surface treatments consisted of: (1) Argon plasma treatment; and (2) Argon plasma treatment with a primer layer of 5% EVAL in 1:1 DMSO:DMF solution applied with the dip-spin process, i.e., centrifugation process, and followed by heat treatments at 120° C. for two hours and 60° C. for 10 hours. The test method used to test adhesion of coatings on stents was a wet flow test, expanding the stents in a Tecoflex tubing at 37° C. of water or saline. Water or saline is then flushed through the stents for 18 hours to simulate blood flow through the stents. The stents were then removed from the Tecoflex with a "stent catcher" and observed under optical microscope for defects.

| Group | Treatment | Flow Rate |
| --- | --- | --- |
| A | None | 50 mL/min |
| B | Argon plasma | 50 mL/min |
| C | Argon plasma + 5% EVAL in 1:1 DMSO:DMF heated at 120° C. for two hours and 60° C. for 10 hours | 50 mL/min |
| D | None | 100 mL/min |
| E | Argon plasma | 100 mL/min |
| F | Argon plasma + 5% EVAL in 1:1 DMSO:DMF heated at 120° C. for two hours and 60° C. for 10 hours | 100 mL/min |

Materials and Equipment
1. 30, 13 mm coated Solo stents, cleaned ultrasonically in IPA for 15 minutes;
2. 30, balloon catheters or subassemblies to expand the stents (3.0×20 mm RX Rocket);
3. 0.67% Actinomycin-D in 5% EVAL with 1:1 THF:DMSO solution;
4. 5% EVAL in 1:1 DMF:DMSO;
5. 3.0 mm, thin walled Tecoflex tubing;
6. Saline;
7. Lint Free Wipes SU 00126 or equivalent;
8. 100% IPA;
9. Oven;
10. Timer;
11. Centrifuge;
12. Plasma Machine (available from Advanced Plasma System);
13. Ultrasonic cleaner;
14. Mettler balance with 0.1 micrograms resolution; and
15. Spray Coater with Fan Air Cap and EFD dispenser (EFD Inc. East Providence R.I.).

Preparation
1. Sonicated the stents in IPA for 15 minutes;
2. Weighed each stent to the nearest microgram;
3. Prepared 5 stent samples:
   A. Groups A and D:
      i. Performed spray-coating process in CER under the following conditions: 3 passes, 3-second spray, no blowing.
      ii. Weighed each sample at the end of the last pass to the nearest microgram.
      iii. Baked the samples for 4 hrs at 60° C.
      iv. Placed the stents into the Tecoflex tubing with a balloon catheter—submerged in 37° C. saline.
   B. Groups B and E:
      i. Placed the samples on a sample holder. Performed argon plasma treatment using plasma machine.
      ii. Performed spray-coating process in CER under the following conditions: 3 passes, 3-second spray, no blow.
      iii. Weighed each sample at the end of the last pass to the nearest microgram.
      iv. Baked the samples for 4 hrs at 60° C.
      v. Placed the stents into the Tecoflex tubing with the balloon catheter—submerged in 37° C. saline.
   C. Groups C and F:
      i. Placed samples flat on a sample holder. Performed argon plasma treatment.
      ii. Used dip-spin process to apply 2% EVAL primer layer, 1:1 DMSO:DMF.
      iii. Baked the stents at 120° C. for two hours.

iv. Baked the stents at 60° C. for ten hours.
v. Performed spray-coating process in CER under the following conditions: 3 passes, 3-second spray, no blow.
vi. Weighed each sample at the end of the last pass to the nearest microgram.
vii. Baked the samples for 4 hrs at 60° C.
viii. Placed the stents into the Tecoflex tubing with a balloon catheter—submerged in 37° C. water.

Test Procedure

Tested three samples from each group. Wet Flow Testing:
1. Expanded the stents into the 3.0 mm Tecoflex tubing in 37° C. saline.
2. Performed wet flow testing for 18 hrs.
3. Removed the stents from the Tecoflex tubing with a stent catcher.
4. Count defects, based on the following categories: Defect type; defect size; defect location; and peel defects on rings 3, 5, and 7.
5. Stent weight could not be a measurable because of the loss of the drug and uptake of water.
6. All test samples were handled with PPE appropriate for drug containing stents.

Data Summary

| Group | Average # of Peel Defects/Stent (3 rings) After Flow Test | Average # Peel Defects/Ring After Flow Test |
| --- | --- | --- |
| A | 18.0 | 6.0 |
| B | 15.3 | 5.1 |
| C | 2.7 | 0.9 |
| D | 14.3 | 4.8 |
| E | 14.0 | 4.7 |
| F | 0.7 | 0.2 |

Discussion

Peel defects are defined as areas where the coating separated from the stent. The number of peel defects were counted on the stents' OD/sidewall on rings 3, 5, and 7. The flow field was on the inner diameter ("ID") of the stents' surface. Some of the damage to the OD surface could have been aggravated by the Tecoflex tubing. The number of peel defects observed on groups C and F (EVAL primer) was clearly lower than the other two test groups, regardless of flow rate. The increased flow rate did not induce more peel defects.

Example 32

Objective

The objective of this experiment was to test the adhesive properties of an Actinomycin-D containing coating on stainless steel stents having an EVAL primer layer. The coated stents were tested in a wet flow test condition of saline heated to 37° C. The number of "peel defects" on a select number of stent rings was observed. A "peel defect" is defined as a location on the stent surface devoid of coating, i.e., bare metal or underlying coating layer that is visible under optical magnification of less than 100×.

| Group | Treatment | Flow Rate |
| --- | --- | --- |
| A | Argon plasma treatment + EVAL primer layer (15% EVAL, 1:1 DMF:DMSO) baked at 140° C. for 2 hours and dried at 60° C. for 2 hours | 50 mL/min |
| B | Argon plasma treatment + EVAL primer layer | 50 mL/min |
| Control | (15% EVAL, 1:1 DMF:DMSO) baked at 120° C. for 2 hours and dried at 60° C. for 10 hours | |

Materials and Equipment
1. 10, 13 mm Solo stents, cleaned ultrasonically in IPA for 15 minutes;
2. 10, balloon catheters or subassemblies to expand the stents;
3. 15% EVAL in 1:1 DMF:DMSO solution;
4. Actinomycin-D solution, 1:1 THF:DMSO with 3:1 EVAL:Act-D;
5. Tecoflex tubing
6. Saline
7. Lint Free Wipes SU 00126 or equivalent
8. 100% IPA
9. Oven
10. Timer
11. Plasma Machine (Advanced Plasma System);
12. Ultrasonic cleaner; and
13. Mettler balance with 0.1 micrograms resolution.

Preparation
1. Sonicated the stents in IPA for 15 minutes.
2. Weighed each stent to the nearest microgram.
3. Prepared 5 stent samples for each group:
    A. Group A (Control):
        i. Placed the samples flat on a sample holder. Performed argon plasma treatment.
        ii. Used dip-spin process, i.e., centrifugation at 6000 rpm for one minute, to apply the EVAL primer layer, 1:1 DMSO:DMF.
        iii. Baked the stents at 140° C. for two hours in the convection oven.
        iv. Took weight measurements of each stent to the nearest microgram.
        v. Baked the stents at 60° C. for two hours in vacuum oven.
        vi. Took weight measurements of each stent to the nearest microgram.
        vii. Performed spray-coating process in CER under the following conditions: 3 passes, 3-second spray, no blow.
        viii. Weighed each sample at the end of the last pass to the nearest microgram.
        ix. Baked samples for 4 hrs at 60° C.
        x. Took weight measurements of each stent to the nearest microgram.
        xi. Placed the stents into the Tecoflex tubing with a balloon catheter—submerged in 37° C. water.
    B. Groups B:
        i. Placed samples flat on sample holder. Performed argon plasma treatment.
        ii. Used dip-spin process at 6000 rpm for one minute to apply EVAL primer layer, 1:1 DMSO:DMF.
        iii. Baked the stents at 120° C. for two hours in the convection oven.
        iv. Took weight measurements on each stent to the nearest microgram.
        v. Baked the stents at 60° C. for ten hours in vacuum oven.
        vi. Took weight measurements for each stent to the nearest microgram.
        vii. Performed spray-coating process in CER at the following conditions: 3 passes, 3-second spray, no blow.
        viii. Weighed each sample at the end of the last pass to the nearest microgram.
        ix. Baked the samples for 4 hrs at 60° C.

x. Took weight measurements of each stent to the nearest microgram.
xi. Placed the stents into the Tecoflex tubing with a balloon catheter—submerged in 37° C. water.

Test Procedure
1. Performed wet flow testing overnight for about 18 hrs.
2. Removed the stents from the Tecoflex tubing with a stent catcher.
3. Counted the defects based on the number of peel defects at rings 3, 5, and 7 on the stents' OD. Count the defects on the ID of the same rings.
4. The weight could not be measured because of the loss of the drug and uptake of water.
5. All test samples were handled with PPE appropriate for drug containing stents.

Data Summary and Results

| Group | # Peel Defects (OD) | Average # of Peel Defects/Ring (OD, rings 3, 5, 7) | # Peel Defects (ID) | Average # of Peel Defects/Ring (ID, rings 3, 5, 7) |
|---|---|---|---|---|
| A | 0 | 0 | 1 | 0.3 |
|  | 0 | 0 | 1 | 0.3 |
|  | 0 | 0 | 1* | 0.3 |
| B | 0 | 0 | 0 | 0 |
|  | 0 | 0 | 0 | 0 |
|  | 0 | 0 | 0 | 0 |

*Defect occurred at a location of a defect in the stent surface.

Example 33

Objective

The objective of this study was to test the adhesive properties of an Actinomycin-D containing coating on stainless steel stents having an EVAL primer layer. The coated stents were tested under wet flow conditions of saline heated to 37° C. The number of "peel defects" on a select number of stent rings was observed. A "peel defect" is defined as a location on the stent surface devoid of coating, i.e., bare metal or an underlying coating layer that is visible under optical magnification of no more than 100×.

| Group | Treatment | Flow Rate |
|---|---|---|
| A Control | None | 50 mL/min |
| B | Argon plasma treatment + EVAL primer layer by dip-spin (2% EVAL, 1:1 DMF:DMSO) baked at 140° C. for 4 hours | 50 mL/min |
| C | EVAL primer layer by dip-spin (2% EVAL, 1:1 DMF:DMSO) baked at 140° C. for 4 hours | 50 mL/min |
| D | Argon plasma treatment + EVAL primer layer by spray (2% EVAL, 1:1 DMF:DMSO) baked at 140° C. for 4 hours | 50 mL/min |
| E | EVAL primer layer by spray (2% EVAL, 1:1 DMF:DMSO) baked at 140° C. for 4 hours | 50 mL/min |

Materials and Equipment
1. 25, 13 mm Solo stents, cleaned ultrasonically in IPA for 15 minutes;
2. 25, balloon catheters or subassemblies to expand the stents;
3. 2% EVAL in 1:1 DMF:DMSO solution;
4. Actinomycin-D solution, 1:1 THF:DMSO with 3:1 EVAL:Act-D;
5. 3.0 mm Tecoflex tubing;
6. Saline;
7. Lint Free Wipes SU 00126 or equivalent;
8. 100% IPA;
9. Convection Oven
10. Timer;
11. Plasma Machine;
12. Ultrasonic cleaner; and
13. Mettler balance with 0.1 micrograms resolution.

Preparation
1. Sonicated the stents in IPA for 15 minutes.
2. Weighed each stent to the nearest microgram.
3. Prepared 5 stent samples for each group.
   A. Group A (Control):
      i. Performed spray-coating process in CER under the following conditions: 3 passes, 3-second spray, no blow.
      ii. Weighed each sample at the end of the last pass to the nearest microgram.
      iii. Baked the samples for 4 hrs at 60° C.
      iv. Took the weight measurements of each stent to the nearest microgram.
      v. Placed the stents into the Tecoflex tubing with the balloon catheter—submerged in 37° C. water.
   B. Group B:
      i. Placed samples flat on sample holder. Perform argon plasma treatment.
      ii. Used dip-spin process to apply EVAL primer layer, 1:1 DMSO:DMF (6000 rpm for one minute).
      iii. Baked the stents at 140° C. for 4 hours in convection oven.
      iv. Took weight measurements on each stent to the nearest microgram.
      v. Performed spray-coating process in CER at the following conditions: 3 passes, 3-second spray, no blow.
      vi. Weighed each sample at the end of the last pass to the nearest microgram.
      vii. Baked the samples for 4 hrs at 60° C.
      viii. Took the weight measurements of each stent to the nearest microgram.
      ix. Placed the stents into the Tecoflex tubing with a balloon catheter—submerged in 37° C. water.
   C. Group C:
      i. Used dip-spin process to apply EVAL primer layer, 1:1 DMSO:DMF (6000 rpm for one minute).
      ii. Baked the stents at 140° C. for four hours in convection oven.
      iii. Took weight measurements on each stent to the nearest microgram.
      iv. Performed spray-coating process in CER under the following conditions: 3 passes, 3-second spray, no blow.
      v. Weighed each sample at the end of the last pass to the nearest microgram.
      vi. Baked the samples for 4 hrs at 60° C.
      vii. Took weight measurements of each stent to the nearest microgram.
      viii. Placed stents into the Tecoflex tubing with a balloon catheter—submerged in 37° C. water.
   D. Group D:
      i. Placed the samples flat on a sample holder. Perform argon plasma treatment.
      ii. Spray coated primer layer (2% EVAL, 1:1 DMF:DMSO) onto the stents. Used 1.5 sec. spray time, 1-2 passes to achieve 10-40 micrograms of coating.
      iii. Baked the stents at 140° C. for 4 hours in the convection oven.
      iv. Took weight measurements of each stent to the nearest microgram.
      v. Performed spray-coating process in CER at the following conditions: 3 passes, 3-second spray, no blow.

vi. Weighed each sample at the end of the last pass to the nearest microgram.
vii. Baked samples for 4 hrs at 60° C.
viii. Took weight measurements of each stent to the nearest microgram.
ix. Placed stents into the Tecoflex tubing with a balloon catheter—submerged in 37° C. water.

E. Group E:
  i. Spray coated primer layer (2% EVAL, 1:1 DMF:DMSO) onto the stents. Used 1.5 sec. spray time, 1-2 passes to achieve 10-40 micrograms of coating.
  ii. Baked the stents at 140° C. for four hours in convection oven.
  iii. Took weight measurements on each stent to the nearest microgram.
  iv. Performed spray-coating process in CER at the following conditions: 3 passes, 3-second spray, no blow.
  v. Weighed each sample at the end of the last pass to the nearest microgram.
  vi. Baked the samples for 4 hrs at 60° C.
  vii. Took weight measurements of each stent to the nearest microgram.
  viii. Placed the stents into the Tecoflex tubing with a balloon catheter—submerged in 37° C. water.

Test Procedure
  1. Performed wet flow testing overnight for about 18 hrs.
  2. Removed stents from the Tecoflex tubing with a stent catcher.
  3. Counted the defects based on the number of peel defects at rings 1, 3, 5, and 7 on the stents' OD. Count the defects on the ID of the same rings.
  4. Stent weight could not be a measurable because of the loss of the drug and uptake of water.
  5. All test samples were handled with PPE appropriate for drug containing stents.

Data Summary and Results

| Group | Defects/Ring (OD) | Defects/Ring (ID) |
|---|---|---|
| Control | 2.67 | 3.00 |
| Dip/Plasma | 0.67 | 0.47 |
| Dip/No Plasma | 0.87 | 0.80 |
| Spray/Plasma | 0.47 | 0.80 |
| Spray/No Plasma | 0.67 | 0.73 |

Discussion

Peel Defects of Primer Coated Stents vs. Untreated Controls

An improved adhesion, based on the number of peel defects, of the drug containing coating to the Tri-Star stent when an EVAL primer layer was applied is illustrated. All four treatment groups displayed significantly fewer peel defects per stent than the untreated control stents. Use of a spray-coated, 2% EVAL solution in 1:1 DMF:DMSO as a primer significantly improved adhesion of Actinomycin-D containing coating to the Tri-Star stents vs. the controls. The spray-coated primer produced slightly higher peel defect counts compared to the dip-spin deposited primer.

Example 34

Objective

The objective of this experiment was to test the adhesive properties of an Actinomycin-D containing coating to stainless steel stents having an EVAL primer layer. More specifically, this experiment attempted to illustrate the effect of different bake times on the final result. The coated stents were tested under wet flow conditions of saline heated to 37° C. The number of "peel defects" on a select number of stent rings was observed.

| Group | Treatment | Flow Rate |
|---|---|---|
| A Control | none | 50 mL/min |
| B | Argon plasma treatment + EVAL primer layer by spray (2% EVAL, 1:1 DMF:DMSO) baked at 140° C. for 15 minutes | 50 mL/min |
| C | Argon plasma treatment + EVAL primer layer by spray (2% EVAL, 1:1 DMF:DMSO) baked at 140° C. for 30 minutes | 50 mL/min |
| D | Argon plasma treatment + EVAL primer layer by spray (2% EVAL, 1:1 DMF:DMSO) baked at 140° C. for 60 minutes | 50 mL/min |
| E | Argon plasma treatment + EVAL primer layer by spray (2% EVAL, 1:1 DMF:DMSO) baked at 140° C. for 120 minutes | 50 mL/min |

Materials and Equipment
  1. 25, 13 mm Solo stents, cleaned ultrasonically in IPA for 15 minutes;
  2. 25, balloon catheters or subassemblies to expand the stents;
  3. 2% EVAL in 1:1 DMF:DMSO solution;
  4. Actinomycin-D solution, 1:1 THF:DMSO with 3:1 EVAL:Act-D;
  5. 30 mm Tecoflex tubing;
  6. Saline;
  7. Lint Free Wipes SU 00126 or equivalent;
  8. 100% IPA;
  9. Convection Oven;
  10. Timer;
  11. Plasma Machine;
  12. Ultrasonic cleaner; and
  13. Mettler balance with 0.1 micrograms resolution.

Preparation
  1. Sonicated stents in IPA for 15 minutes.
  2. Weighed each stent to the nearest microgram.
  3. Prepared 5 stent samples for each group.
    A. Group A (Control):
      i. Performed spray-coating process in CER under the following conditions: 3 passes, 3-second spray, no blow.
      ii. Weighed each sample at the end of the last pass to the nearest microgram.
      iii. Baked the samples for 240 minutes at 50° C.
      iv. Took weight measurements of each stent to the nearest microgram.
      v. Placed the stents into the Tecoflex tubing with a balloon catheter—submerged in 37° C. water.
    B. Group B:
      i. Placed samples flat on sample holder. Perform argon plasma treatment.
      ii. Spray coated primer layer (2% EVAL, 1:1 DMF:DMSO) onto stents. Used 1.5 sec. spray time, 1-2 passes to achieve 10-40 micrograms of coating.
      iii. Baked the stents at 140° C. for 15 minutes in the convection oven.
      iv. Took weight measurements on each stent to the nearest microgram.
      v. Performed spray-coating process in CER under the following conditions: 3 passes, 3-second spray, no blow.
      vi. Weighed each sample at the end of the last pass to the nearest microgram.
      vii. Baked the samples for 240 minutes at 50° C.

viii. Took weight measurements of each stent to the nearest microgram.
ix. Placed stents into the Tecoflex tubing with a balloon catheter—submerged in 37° C. water.

C. Group C:
i. Placed the samples flat on sample holder. Perform argon plasma treatment.
ii. Spray coated primer layer (2% EVAL, 1:1 DMF:DMSO) onto stents. Used 1.5 sec. spray time, 1-2 passes to achieve 10-40 micrograms of coating.
iii. Baked the stents at 140° C. for 30 minutes in the convection oven.
iv. Took weight measurements on each stent to the nearest microgram.
v. Performed spray-coating process in CER under the following conditions: 3 passes, 3-second spray, no blow.
vi. Weighed each sample at the end of the last pass to the nearest microgram.
vii. Baked the samples for 240 minutes at 50° C.
viii. Took weight measurements of each stent to the nearest microgram.
ix. Placed stents into the Tecoflex tubing with a balloon catheter—submerged in 37° C. water.

D. Group D:
i. Placed samples flat on sample holder. Perform argon plasma treatment.
ii. Spray coated primer layer (2% EVAL, 1:1 DMF:DMSO) onto stents. Used 1.5 sec. spray time, 1-2 passes to achieve 10-40 micrograms of coating.
iii. Baked the stents at 140° C. for 60 minutes in the convection oven.
iv. Took weight measurements on each stent to the nearest microgram.
v. Performed spray-coating process in CER under the following conditions: 3 passes, 3-second spray, no blow.
vi. Weighed each sample at the end of the last pass to the nearest microgram.
vii. Baked the samples for 240 minutes at 50° C.
viii. Took weight measurements of each stent to the nearest microgram.
ix. Placed stents into the Tecoflex tubing with a balloon catheter—submerged in 37° C. water.

E. Group E:
i. Placed samples flat on sample holder. Perform argon plasma treatment.
ii. Spray coated primer layer (2% EVAL, 1:1 DMF:DMSO) onto stents. Used 1.5 sec. spray time, 1-2 passes to achieve 10-40 micrograms of coating.
iii. Baked the stents at 140° C. for 120 minutes in the convection oven.
iv. Took weight measurements on each stent to the nearest microgram.
v. Performed spray-coating process in CER at the following conditions: 3 passes, 3-second spray, no blow.
vi. Weighed each sample at the end of the last pass to the nearest microgram.
vii. Baked samples for 240 minutes at 50° C.
viii. Took weight measurements of each stent to the nearest microgram.
ix. Placed stent into the Tecoflex tube with balloon catheter—submerged in 37° C. water.

Test Procedure
1. Performed wet flow testing overnight for about 18 hrs.
2. Removed the stents from the Tecoflex tubing with a stent catcher.
3. Counted the defects based on the number of peel defects at rings 3, 5, and 7 on the stents' OD. Count the defects on the ID of the same rings.
4. Stent weight could not be a measurable because of the loss of the drug and uptake of water.
5. All test samples were handled with PPE appropriate for drug containing stents.

Data Summary and Results

| Group | Total Defects per Stent |
| --- | --- |
| Control | 3.33 |
| 15 min bake | 1.00 |
| 30 min bake | 3.00 |
| 60 min bake | 1.67 |
| 120 min bake | 1.33 |

Discussion

The control group with no primer layer had significantly more peel defects as compared to the treatment groups with a primer layer. The groups with shorter baking times (15 and 30 minutes) had higher defect counts than the groups with longer baking times.

Example 35

Objective

The objective of this experiment was to test the adhesive properties of an Actinomycin-D containing coating on stainless steel stents having an EVAL primer layer. More specifically, different solvent systems (e.g., THF and DMF) were evaluated. The coated stents were tested under wet flow conditions of saline heated to 37° C. The number of "peel defects" on a select number of stent rings was observed.

| Group | Treatment | Flow Rate |
| --- | --- | --- |
| A Control | none | 50 mL/min |
| B | Argon plasma treatment + EVAL primer layer by spray (2% EVAL, 1:1 DMF:DMSO) baked at 140° C. for 15 minutes | 50 mL/min |
| C | Argon plasma treatment + EVAL primer layer by spray (2% EVAL, 1:1 DMF:DMSO) baked at 140° C. for 60 minutes | 50 mL/min |
| D | Argon plasma treatment + EVAL primer layer by spray (2% EVAL, 1:1 DMF:DMSO) baked at 140° C. for 240 minutes | 50 mL/min |
| E | Argon plasma treatment + EVAL primer layer by spray (2% EVAL, 1:1 THF:DMSO) baked at 140° C. for 60 minutes | 50 mL/min |

Materials and Equipment
1. 25, 13 mm Solo stents, cleaned ultrasonically in IPA for 15 minutes;
2. 25, balloon catheters or subassemblies to expand the stents;
3. 2% EVAL in 1:1 DMF:DMSO solution;
4. 2% EVAL in 1:1 THF:DMSO solution;
5. Actinomycin-D solution, 1:1 THF:DMSO with 3:1 EVAL:Act-D, 2% EVAL;
6. 3.0 mm Tecoflex tubing;
7. Saline;
8. Lint Free Wipes SU 00126 or equivalent;
9. 100% IPA;
10. Convection Oven;
11. Timer;
12. Plasma Machine;

13. Ultrasonic cleaner; and
14. Mettler balance with 0.1 micrograms resolution.

Preparation
1. Sonicated stents in IPA for 15 minutes.
2. Weighed each stent to the nearest microgram.
3. Prepared 5 stent samples for each group.
   A. Group A (Control):
      i. Performed spray-coating process in CER under the following conditions: 3 passes, 3-second spray, no blow.
      ii. Weighed each sample at the end of the last pass to the nearest microgram.
      iii. Baked samples for 240 minutes at 50° C.
      iv. Took weight measurements of each stent to the nearest microgram.
      v. Placed the stents into the Tecoflex tubing with a balloon catheter—submerged in 37° C. water.
   B. Group B:
      i. Placed samples flat on a sample holder. Performed argon plasma treatment.
      ii. Spray coated the primer layer (2% EVAL, 1:1 DMF:DMSO) onto the stents. Used 1.5 sec. spray time, 1-2 passes to achieve 10-40 micrograms of coating.
      iii. Baked the stents at 140° C. for 15 minutes in the convection oven.
      iv. Took weight measurements of each stent to the nearest microgram.
      v. Performed spray-coating process in CER under the following conditions: 3 passes, 3-second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the Tecoflex tubing with a balloon catheter—submerged in 37° C. water.
   C. Group C:
      i. Placed samples flat on a sample holder. Performed argon plasma treatment.
      ii. Spray coated the primer layer (2% EVAL, 1:1 DMF:DMSO) onto the stents. Used 1.5 sec. spray time, 1-2 passes to achieve 10-40 micrograms of coating.
      iii. Baked the stents at 140° C. for 60 minutes in the convection oven.
      iv. Took weight measurements of each stent to the nearest microgram.
      v. Performed spray-coating process in CER under the following conditions: 3 passes, 3-second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the Tecoflex tubing with a balloon catheter—submerged in 37° C. water.
   D. Group D:
      i. Placed samples on flat on a sample holder. Performed argon plasma treatment.
      ii. Spray coated the primer layer (2% EVAL, 1:1 DMF:DMSO) onto the stents. Used 1.5 sec. spray time, 1-2 passes to achieve 10-40 micrograms of coating.
      iii. Baked the stents at 140° C. for 240 minutes in the convection oven.
      iv. Took weight measurements of each stent to the nearest microgram.
      v. Performed spray-coating process in CER at the following conditions: 3 passes, 3-second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the Tecoflex tubing with a balloon catheter—submerged in 37° C. water.
   E. Group E:
      i. Placed samples flat on a sample holder. Perform argon plasma treatment.
      ii. Spray coated the primer layer (2% EVAL, 1:1 THF:DMSO) onto the stents. Used 1.5 sec. spray time, 1-2 passes to achieve 10-40 micrograms of coating.
      iii. Baked the stents at 140° C. for 60 minutes in the convection oven.
      iv. Took weight measurements of each stent to the nearest microgram.
      v. Performed spray-coating process in CER under the following conditions: 3 passes, 3 second spray, no blow.
      vi. Weighed each sample at the end of the last pass to the nearest microgram.
      vii. Baked the samples for 240 minutes at 50° C.
      viii. Took weight measurements of each stent to the nearest microgram.
      ix. Placed the stents into the Tecoflex tubing with a balloon catheter—submerged in 37° C. water.

Test Procedure
1. Performed wet flow testing overnight for about 18 hrs.
2. Removed the stents from the Tecoflex tubing with a stent catcher.
3. Counted the defects, based on the number of peel defects at rings 3, 5, and 7 on the stents' OD. Counted defects on the ID of the same rings.
4. The weight of the stents could not be a measurable because of the loss of the drug and uptake of water.
5. All test samples were handled with PPE appropriate for drug containing stents.

Data Summary and Results

| Group | Total Defects per Stent |
| --- | --- |
| No primer control | 0.00 |
| 15 min. bake | 0.00 |
| 60 min. bake | 0.33 |
| 240 min. bake | 0.00 |
| THF, 15 min. bake | 0.00 |

Example 36

Objective

The objective of this experiment was to test the adhesive properties of an Actinomycin-D containing coating on stainless steel stents having an EVAL primer layer made from a DMSO:THF solution applied to the stents. The coated stents were tested under wet flow conditions of saline heated to 37° C. The number of "peel defects" on a select number of stent rings was observed.

| Group | Treatment | Drying Time (min.) |
| --- | --- | --- |
| A | Argon plasma treatment + EVAL primer | 15 |
| B | Argon plasma treatment + EVAL primer | 30 |
| C | Argon plasma treatment + EVAL primer | 60 |

| Group | Treatment | Drying Time (min.) |
|---|---|---|
| D | Argon plasma treatment + EVAL primer | 90 |
| E | Argon plasma treatment + EVAL primer | 120 |

Materials and Equipment
1. 10, 13 mm SOLO stents, cleaned ultrasonically in IPA for 15 minutes;
2. 2% EVAL in 1:1 THF:DMSO solution;
3. 10 Balloon catheters or subassemblies to expand the stents;
4. Actinomycin-D solution, 1:1 THF:DMSO with 1:3 Act-D:EVAL, 2% EVAL;
5. 4.0 mm Tecoflex tubing;
6. Saline;
7. Lint Free Wipes SU 00126 or equivalent;
8. 100% IPA;
9. Convection Oven;
10. Timer;
11. Plasma Machine;
12. Ultrasonic cleaner;
13. Mettler balance with 0.1 microgram resolution;
14. Spray/bake mandrels and tips;
15. Flow Meter, N1429;
16. Microscope, minimum magnification 50×;
17. EFD controller with spray apparatus without translational stage; and
18. EFD controller with spray apparatus with translational stage.

Preparation
1. Sonicated the stents in IPA for 15 minutes.
2. Weighed each stent to the nearest microgram.
3. Prepare the stent samples for each group.
   A. Primer Coat
   i. Placed samples on sample holder. Performed argon plasma treatment.
   ii. Sprayed the primer layer (2% EVAL, 1:1 THF:DMSO) onto the stents with translational spray coater. Used 1.5 sec. for the spray time and speed 7 to achieve 10-40 μg of coating.
   iii. Baked the stents at 140° C. for the specified time in the convection oven.
   iv. Weighed the stents and recorded measurements to the nearest microgram.
   B. Drug Coat
   i. Sprayed the stents with a 3:1, EVAL:Act-D, 2% EVAL, 1:1 DMSO:THF solution for three seconds per pass for three passes. After each spray pass, dried the stents in the convection oven for 15 minutes at 50° C.
   ii. Weighed the stents and recorded measurements. If the drug coat weight matched the target weight, the stents were returned to the oven for 240 minutes. If weight gain did not match, the stents were returned to the glove box for additional spray coat application. Spray time on subsequent passes was adjusted to achieve target weight.
4. Wet Flow Test Sample Preparation
   A. Crimped the stents onto the balloon catheters.
   B. Inflated the stents to 4.0 mm in the Tecoflex tubing with the balloon catheters—submerged in 37° C. water.
   C. Disposed Act-D contaminated water as hazardous waste.

Test Method/Procedure
1. Set flow rate at 50 ml/min.
2. Performed wet flow testing overnight for about 18 hrs.
3. Removed the stents from the Tecoflex tubing with a stent catcher.
4. Counted defects, based on the number of peel defects at rings 1, 3, 5, 7, and 10 on the stents' OD. Counted defects on the ID of the same rings.
5. All test samples were handled with PPE appropriate for drug containing stents.

Data Summary and Results

| Drying Time (min.) | Total Defects per Stent | Total Defects per Stent (end rings) | Total Defects per Stent (middle rings) |
|---|---|---|---|
| 15 | 0.0 | 0.0 | 0.0 |
| 30 | 2.0 | 2.0 | 0.0 |
| 60 | 1.0 | 1.0 | 0.0 |
| 90 | 0.0 | 0.0 | 0.0 |
| 120 | 0.5 | 0.5 | 0.0 |

While particular embodiments of the present invention have been shown and described, it will be obvious to those skilled in the art that changes and modifications can be made without departing from this invention in its broader aspects and, therefore, the appended claims are to encompass within their scope all such changes and modifications as fall within the true spirit and scope of this invention.

The invention claimed is:

1. A stent comprising a coating, the coating comprising:
   a) a reservoir region comprising a polymer and a drug blended with or dispersed in the polymer; and
   b) a primer region free from any drugs located between the reservoir region and the surface of the stent, the primer region comprising a material comprising an inorganic polymer selected from the group consisting of (3-glycidoxypropyl)methyldiethoxysilane, tetra-iso-propyl titanate, tetra-n-butyl titanate, n-propyl zirconate, n-butyl zirconate, and combinations thereof.

2. The stent of claim 1, wherein the surface of the stent comprises a chromium oxide layer.

3. The stent of claim 1, wherein the inorganic polymer is (3-glycidoxypropyl)methyldiethoxysilane.

4. The stent of claim 1, wherein the inorganic polymer is selected from the group consisting of tetra-iso-propyl titanate, tetra-n-butyl titanate, and combinations thereof.

5. The stent of claim 1, wherein the inorganic polymer is selected from the group consisting of n-propyl zirconate, n-butyl zirconate, and combinations thereof.

6. The stent of claim 1, wherein the surface of the stent is metallic.

7. The stent of claim 1, wherein the reservoir region comprises a combination of polymers.

8. The stent of claim 1, wherein the surface of the stent is stainless steel.

9. A stent comprising a coating, the coating comprising:
   a) a reservoir region comprising a drug; and
   b) a primer region free from any drugs located between the reservoir region and the surface of the stent, the primer region comprising an inorganic polymer selected from the group consisting of (3-glycidoxypropyl)-methyldiethoxysilane, tetra-iso-propyl titanate, tetra-n-butyl titanate, n-propyl zirconate, n-butyl zirconate, and combinations thereof.

10. The stent of claim 9, wherein the inorganic polymer is (3-glycidoxypropyl)methyldiethoxysilane.

11. The stent of claim 9, wherein the inorganic polymer is selected from the group consisting of tetra-iso-propyl titanate, tetra-n-butyl titanate, and combinations thereof.

12. The stent of claim 9, wherein the inorganic polymer is selected from the group consisting of n-propyl zirconate, n-butyl zirconate, and combinations thereof.

13. The stent of claim 9, wherein the surface of the stent is metallic.

14. The stent of claim 13, where the surface of the stent is stainless steel.

15. An implantable device comprising a coating, the coating comprising:
   a) a reservoir region comprising a polymer and a drug blended with or dispersed in the polymer; and
   b) a primer region free from any drugs located between the reservoir region and the surface of the device, the primer region comprising a material comprising an inorganic polymer selected from the group consisting of (3-glycidoxypropyl)methyldiethoxysilane, n-propyl zirconate, n-butyl zirconate, and combinations thereof.

16. The implantable device of claim 15, wherein the inorganic polymer is (3-glycidoxypropyl)methyldiethoxysilane.

17. The implantable device of claim 15, wherein the inorganic polymer is selected from the group consisting of n-propyl zirconate, n-butyl zirconate, and combinations thereof.

* * * * *